US010898720B2

(12) United States Patent
Christie et al.

(10) Patent No.: US 10,898,720 B2
(45) Date of Patent: Jan. 26, 2021

(54) IMPEDANCE SENSING

(71) Applicant: Medtronic, Inc., Minneapolis, MN (US)

(72) Inventors: Melissa G. T. Christie, Ham Lake, MN (US); Ronald A. Drake, St. Louis Park, MN (US); Vladimir P. Nikolski, Blaine, MN (US); Bushan K. Purushothaman, Plymouth, MN (US); Xusheng Zhang, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 112 days.

(21) Appl. No.: 16/161,534

(22) Filed: Oct. 16, 2018

(65) Prior Publication Data

US 2019/0111268 A1   Apr. 18, 2019

Related U.S. Application Data

(60) Provisional application No. 62/573,436, filed on Oct. 17, 2017.

(51) Int. Cl.
*A61B 5/00* (2006.01)
*A61B 5/04* (2006.01)
(Continued)

(52) U.S. Cl.
CPC ...... *A61N 1/36521* (2013.01); *A61B 5/04011* (2013.01); *A61B 5/0456* (2013.01);
(Continued)

(58) Field of Classification Search
CPC ............. A61B 5/0464; A61B 5/04011; A61B 2562/043; A61B 2562/0271;
(Continued)

(56) References Cited

U.S. PATENT DOCUMENTS 4,291,699 A * 9/1981 Geddes ............... A61B 5/0535
607/6
5,335,668 A   8/1994 Nardella
(Continued)

FOREIGN PATENT DOCUMENTS

EP   2371280 A1   10/2011

OTHER PUBLICATIONS

Burkland et al., "Near-Field Impedance Accurately Distinguishes Among Pericardial, Intracavitary, and Anterior Mediastinal Position", Journal of Cardiovascular Electrophysiology, Jun. 2017, 10 pages.

(Continued)

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

In some examples, a medical device system includes an electrode. The medical device system may include impedance measurement circuitry coupled to the electrode, the impedance measurement circuitry may be configured to generate an impedance signal indicating impedance proximate to the electrode. The medical device system may include processing circuitry that may be configured to identify a first component of the impedance signal. The first component of the impedance signal may be correlated to a cardiac event. The processing circuitry may be configured to determine that the cardiac event occurred based on the identification of the first component of the impedance signal.

23 Claims, 10 Drawing Sheets

(51) Int. Cl.

| | |
|---|---|
| *A61B 5/0452* | (2006.01) |
| *A61B 5/0456* | (2006.01) |
| *A61B 5/046* | (2006.01) |
| *A61B 5/0464* | (2006.01) |
| *A61B 5/053* | (2006.01) |
| *A61B 5/08* | (2006.01) |
| *A61B 5/11* | (2006.01) |
| *A61N 1/04* | (2006.01) |
| *A61N 1/05* | (2006.01) |
| *A61N 1/362* | (2006.01) |
| *A61N 1/365* | (2006.01) |
| *A61N 1/37* | (2006.01) |
| *A61N 1/38* | (2006.01) |
| *A61B 5/0468* | (2006.01) |
| *A61N 1/39* | (2006.01) |

(52) U.S. Cl.
CPC ........ *A61B 5/0464* (2013.01); *A61B 5/04525* (2013.01); *A61B 5/0816* (2013.01); *A61B 5/1116* (2013.01); *A61B 5/1118* (2013.01); *A61B 5/4836* (2013.01); *A61B 5/7257* (2013.01); *A61N 1/046* (2013.01); *A61N 1/3712* (2013.01); *A61N 1/3716* (2013.01); *A61N 1/385* (2013.01); *A61N 1/3918* (2013.01); *A61N 1/3943* (2013.01); *A61N 1/3956* (2013.01); *A61N 1/3968* (2013.01); *A61N 1/3987* (2013.01); *A61N 1/39622* (2017.08); *A61B 5/046* (2013.01); *A61B 5/0538* (2013.01); *A61B 5/1102* (2013.01); *A61B 5/725* (2013.01); *A61B 2562/0204* (2013.01); *A61B 2562/0219* (2013.01); *A61B 2562/0271* (2013.01); *A61B 2562/043* (2013.01); *A61N 1/0504* (2013.01); *A61N 1/3621* (2013.01); *A61N 1/36585* (2013.01)

(58) Field of Classification Search
CPC .... A61B 2562/0219; A61B 2562/0204; A61B 5/7257; A61B 5/725; A61B 5/4836; A61B 5/1118; A61B 5/1116; A61B 5/1102; A61B 5/0816; A61B 5/0538; A61B 5/046; A61B 5/0456; A61B 5/04525; A61B 5/7235; A61B 5/7253; A61B 5/0468; A61B 5/053; A61N 1/3956; A61N 1/3621; A61N 1/3943; A61N 1/046; A61N 1/3987; A61N 1/3968; A61N 1/3918; A61N 1/385; A61N 1/3716; A61N 1/3712; A61N 1/36585; A61N 1/0504; A61N 1/39622
See application file for complete search history.

(56) References Cited

U.S. PATENT DOCUMENTS

| | | |
|---|---|---|
| 5,536,267 A | 7/1996 | Edwards et al. |
| 5,792,204 A | 8/1998 | Snell |
| 6,546,935 B2 | 4/2003 | Hooven |
| 6,714,806 B2 | 3/2004 | Iaizzo et al. |
| 7,599,730 B2 | 10/2009 | Hunter et al. |
| 7,706,865 B1* | 4/2010 | Snell .................... A61B 5/7203 600/509 |
| 7,991,484 B1 | 8/2011 | Sengupta et al. |
| 8,180,454 B2 | 5/2012 | Greenberg et al. |
| 10,143,839 B1 | 12/2018 | Christie et al. |
| 2003/0199938 A1 | 10/2003 | Smits et al. |
| 2004/0133113 A1 | 7/2004 | Krishnan |
| 2004/0204734 A1 | 10/2004 | Wagner et al. |
| 2006/0069419 A1 | 3/2006 | Sweeney et al. |
| 2007/0043394 A1* | 2/2007 | Zhang ................ A61N 1/36521 607/8 |
| 2008/0004667 A1* | 1/2008 | Arcot-Krishnamurthy ................ A61N 1/36514 607/17 |
| 2008/0065061 A1 | 3/2008 | Viswanathan |
| 2009/0299422 A1* | 12/2009 | Ousdigian .............. A61B 5/053 607/5 |
| 2010/0113963 A1 | 5/2010 | Smits et al. |
| 2010/0179411 A1* | 7/2010 | Holmstrom ............ A61B 5/053 600/374 |
| 2011/0125049 A1 | 5/2011 | Nabutovsky et al. |
| 2011/0190654 A1* | 8/2011 | Hettrick ............ A61N 1/36521 600/547 |
| 2011/0245698 A1* | 10/2011 | Wang ................ A61N 1/39622 600/509 |
| 2014/0316429 A1 | 10/2014 | Smits et al. |
| 2016/0144192 A1 | 5/2016 | Sanghera et al. |

OTHER PUBLICATIONS

Trebbels et al., "Real-Time Cannula Navigation in Biological Tissue with High Temporal and Spatial Resolution Based on Impedance Spectroscopy", 32 Annual International Conference of the IEEE EMBS, Buenos Aires, Argentina, Aug. 31-Sep. 4, 2010, 4 pages.
Hsia et al., Novel Minimally Invasive, Intrapericardial Implantable Cardioverter Defibrillator Coil System: A Useful Approach to Arrhythmia Theraphy in Children, Ann Thorac Surg, 2009 vol. 87, 6 pages.
(PCT/US2018/056172) PCT Notification of Transmittal of the International Search Report and the Written Opinion of the International Searching Authority, dated Feb. 1, 2019, 11 pages.
International Preliminary Report on Patentability from International Application No. PCT/US2018/056172, dated Apr. 21, 2020, 6 pp.

* cited by examiner

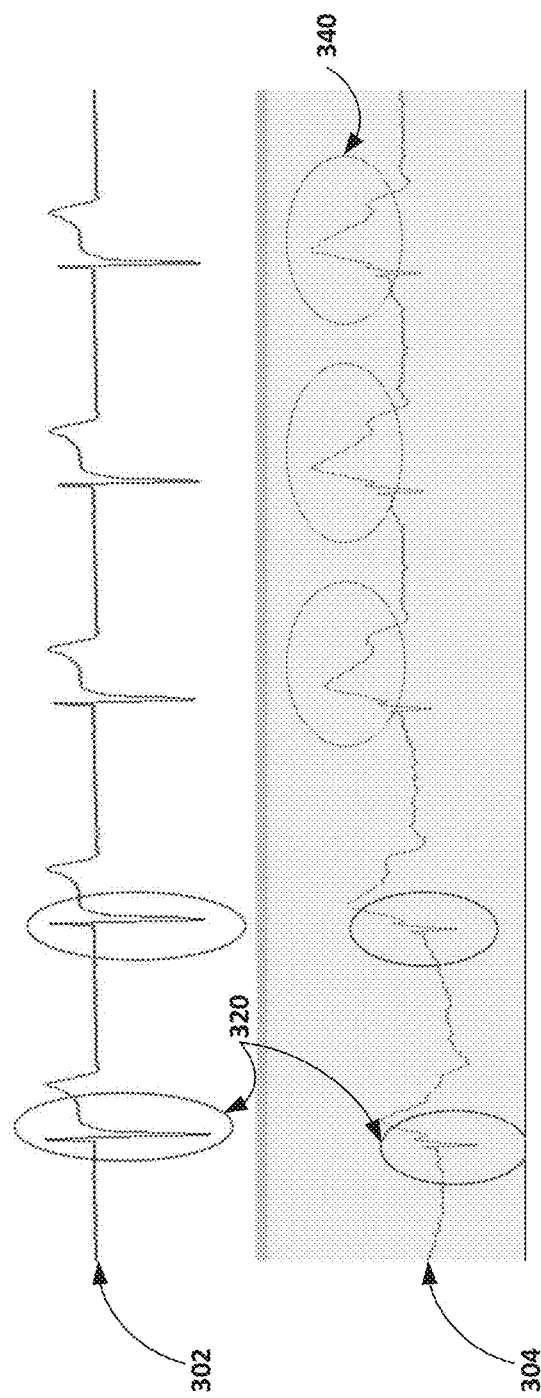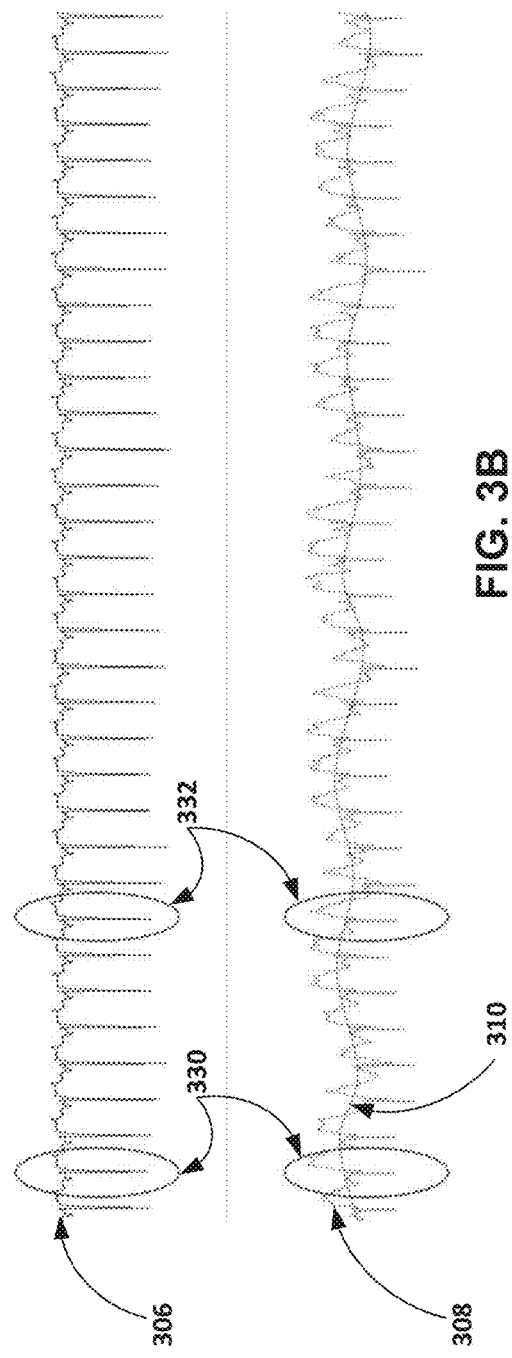

IMPEDANCE SENSING

This application claims the benefit of U.S. Provisional Application No. 62/573,436, filed on Oct. 17, 2017, entitled "IMPEDANCE SENSING," the content of which is incorporated herein by reference in its entirety.

TECHNICAL FIELD

This disclosure relates to medical devices, and more particularly, to techniques for sensing impedance with implantable medical devices.

BACKGROUND

Implantable pulse generators have been used to provide electrical stimulation to organs, tissues, muscles, nerves, or other parts of a patient's body. One example of electrical stimulation is cardiac pacing. Cardiac pacing includes electrically stimulating the heart when the heart's natural pacemaker or conduction system fails to provide synchronized atrial and ventricular contractions at appropriate rates and intervals for the patient's needs. When the patient's heart is beating too slowly, bradycardia pacing increases the rate at which the patient's heart contracts to provide relief from symptoms associated with bradycardia.

Malignant tachyarrhythmia, for example, ventricular fibrillation (VF), is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes. Implantable cardioverter-defibrillators (ICDs), with or without cardiac pacing capabilities, may provide electrical shocks configured to terminate tachyarrhythmias. Cardiac pacing may also provide electrical stimulation intended to suppress or convert tachyarrhythmias. This may supply relief from symptoms, and prevent or terminate arrhythmias that could lead to sudden cardiac death or the need to be treated with high voltage defibrillation or cardioversion shocks.

Traditional implantable pulse generators, such as cardiac pacemakers and ICDs include a housing that encloses a pulse generator and other electronics, and is implanted subcutaneously in the chest of the patient. The housing is connected to one or more implantable medical electrical leads. The electrical lead includes one or more electrodes on a distal portion of the lead that is implanted inside the patient, such as inside the patient's heart (e.g., such that at least one of the electrodes contacts the endocardium), within vasculature near the heart (e.g., within the coronary sinus), or attached to the outside surface of the heart (e.g., in the pericardium or epicardium).

SUMMARY

This disclosure, among other things, describes systems and techniques for sensing impedance. One aspect of this disclosure includes techniques for identifying one or more components of an impedance signal. The one or more components may be correlated to or otherwise associated with cardiac events, such as a cardiac depolarization or other electrical cardiac events, or other hemodynamic events.

An implantable medical device may generate an impedance signal indicative of impedance proximate to an electrode coupled to the device. The implantable medical device may include an extravascular ICD, an insertable cardiac monitor, or other types of devices. In some examples, e.g., in the case of an extravascular ICD, at least one of the electrodes may be positioned within the substernal space. The implantable medical device, or another device in a medical device system including the implantable medical device, may determine the occurrence of the cardiac event based on the one or more components of the impedance signal.

The techniques described herein include determining a variety of information based on the impedance signal, e.g., detected via an electrode in the substernal space. For example, the medical device system may determine volume changes of a patient's heart over time based on the impedance signal (e.g., based on impedance waveform oscillations or morphology). In an example, the medical device system may determine respiration information based on the impedance signal. In another example, the medical device system may determine other cardiac information. In some examples, the medical device system may determine information based on the impedance signal that is normally associated with other types of signals, e.g., a cardiac electrogram (EGM) signal.

One type of signal that is used to determine cardiac information is the cardiac EGM. By using the systems and techniques described herein, the heart's EGM status may be determined by the impedance signal. In some examples, this may not require an actual EGM signal. In other examples, impedance information and EGM information may be used together, such as to confirm a cardiac event determined based on a first signal (e.g., the EGM signal) and confirmed based on a second signal (e.g., the impedance signal). Some other examples of signals include a heart sound signal, an accelerometer signal (e.g., a three-axis accelerometer signal), and an electrocardiogram (EKG).

The impedance signal may be used by one or more devices to determine physiological information of the patient. One aspect of this disclosure includes injecting a signal used to determine impedance into an extracardiovascular location (e.g., the substernal space) within the patient. The extracardiovascular location may include subcutaneous or substernal locations. Subcutaneous leads do not intimately contact the heart, but instead reside in a plane of tissue between the skin and sternum. Likewise, substernal leads do not intimately contact the heart, but instead reside in a plane of tissue between the sternum and the heart. However, although described primarily herein with respect to extracardiovascular locations, the techniques described herein may be applied to impedance signals from electrodes at any locations, including transvenous or other vascular locations, or intracardiac location (e.g., electrode may be advanced through a vein of a patient).

By using the systems and techniques described herein, heart activity (e.g., heart motion, heart sounds, or heart electrical activity) may be determined and used to deliver appropriate therapy more reliably to the patient. Therapy may include, for example, antitachycardia pacing (ATP) or defibrillation.

Additionally, by using impedance information (e.g., from a carrier signal between two electrodes, at least one of which is in the substernal space), cardiac events may be detected with better specificity and sensitivity, in some situations. However, the systems and techniques described herein may be utilized in other anatomical spaces, such as within the heart or proximate to other organs, or with external electrodes. For example, the medical device system described herein may be used with left ventricular lead implants such as to provide impedance mapping functionality, with an electrocardiogram (ECG) belt to provide more information during a medical diagnosis or therapy, or with another mapping system (e.g., a CardioInsight™ Noninvasive 3D Mapping System, available from Medtronic plc, of Dublin, Ireland).

In an example, this disclosure is directed to a method for determining an occurrence of a cardiac event of a patient. The method may comprise: generating, by impedance measurement circuitry coupled to an electrode, an impedance signal indicating impedance proximate to the electrode; identifying, by processing circuitry, a first component of the impedance signal, the first component correlated to a cardiac event; and determining, by the processing circuitry, that the cardiac event occurred based on the identification of the first component of the impedance signal.

In an example, this disclosure is directed to a medical device system comprising: an electrode; impedance measurement circuitry coupled to the electrode, the impedance measurement circuitry configured to generate an impedance signal indicating impedance proximate to the electrode; and processing circuitry configured to: identify a first component of the impedance signal, the first component correlated to a cardiac event; and determine that the cardiac event occurred based on the identification of the first component of the impedance signal.

A medical device system comprising an electrode; impedance measurement circuitry coupled to the electrode, the impedance measurement circuitry configured to generate an impedance signal indicating impedance proximate to the electrode; therapeutic signal generation circuitry configured to generate and deliver an electrical stimulation; and processing circuitry configured to identify a plurality of cardiac events within the impedance signal; detect a cardiac arrhythmia based on the plurality of identified cardiac events within the impedance signal; control the therapeutic signal generation circuitry to generate the electrical stimulation therapy in response to detection of the cardiac arrhythmia.

A method comprising generating an impedance signal indicating impedance proximate an electrode; identifying a plurality of cardiac events within the impedance signal; detecting a cardiac arrhythmia based on the plurality of identified cardiac events within the impedance signal; and controlling the therapeutic signal generation circuitry to generate the electrical stimulation therapy in response to detecting cardiac arrhythmia.

A medical device system comprising an electrode; impedance measurement circuitry coupled to the electrode, the impedance measurement circuitry configured to generate an impedance signal indicating impedance proximate to the electrode; and processing circuitry configured to analyze at least one of an amplitude and a slope in the impedance signal; detect a change in at least one of the amplitude or the slope in the impedance signal that exceeds a respective threshold; and detect a cardiac event in response to detecting the change in at least one of the amplitude or the slope of the impedance signal that exceeds the respective threshold.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

FIGS. 3A and 3B illustrate graphs of example physiological signals, including impedance signals.

Figure 1A:
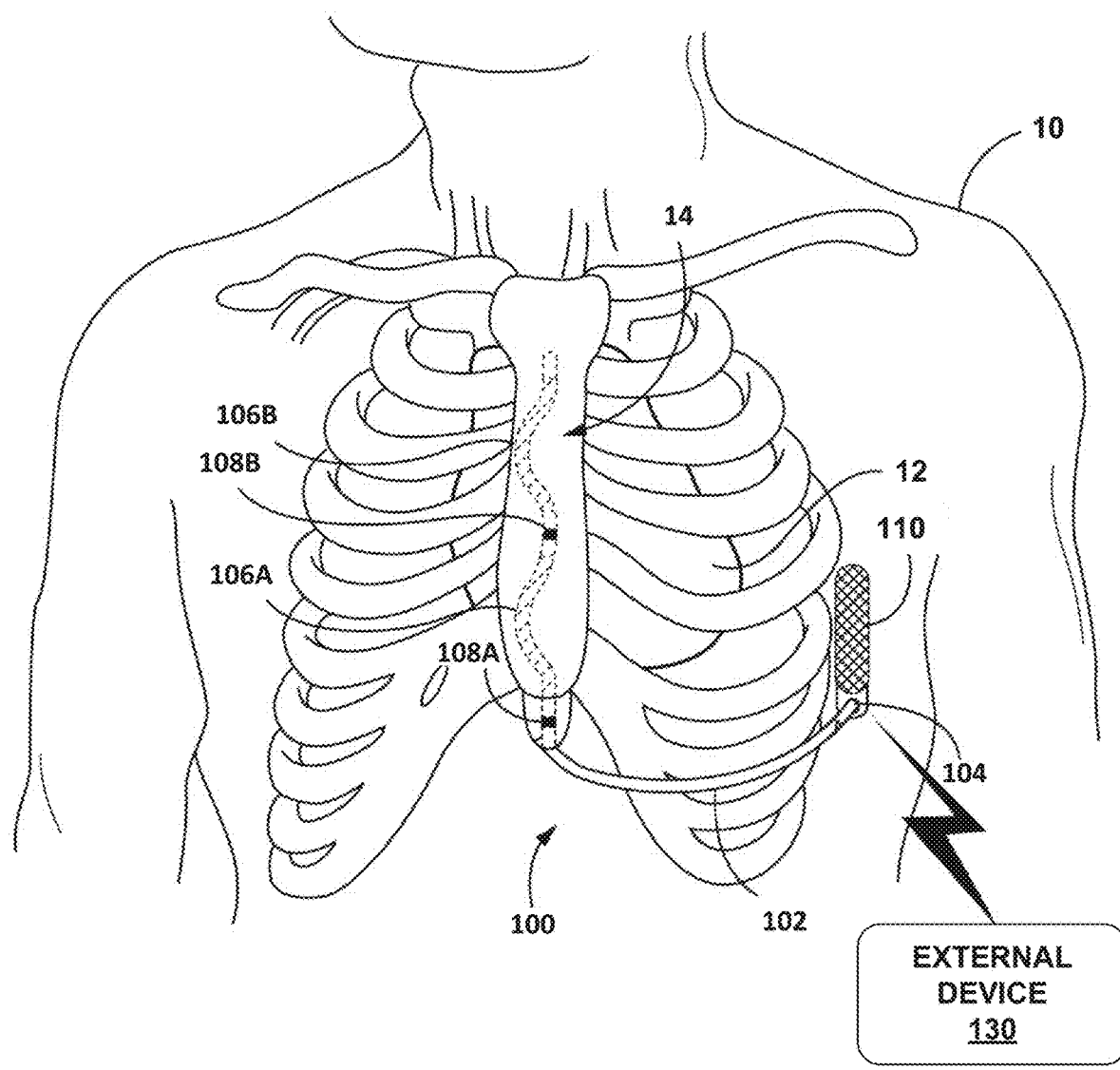
FIGS. 1A-1C are front-view, side-view, and top-view conceptual drawings, respectively, illustrating an example medical device system in conjunction with a patient.

The details of one or more examples of this disclosure are set forth in the accompanying drawings and the description below. Other features, objects, and advantages of this disclosure will be apparent from the description and drawings, and from the claims.

DETAILED DESCRIPTION

In this disclosure, techniques, systems, devices, components, assemblies, and methods for determining a physiological event of a patient (e.g., an electrical cardiac event or other hemodynamic event) based on an impedance signal are described. Additionally, techniques for detecting other physiological events and/or determining other physiological information, e.g., respiration events or information, based on the impedance signal are also described.

In general, a medical device system may include one or more electrodes, such as placed on the lead or such as a housing electrode. Impedance measurement circuitry may use two or more electrodes to generate an impedance signal therebetween. In some examples, the impedance signal is indicative of the impedance proximate to one of these electrodes. The impedance signal may be indicative of impedance across a vector between the two electrodes, in some examples. In an example, the impedance signal may be indicative of the impedance proximate to the electrode on the lead, including when the electrode on the lead is a cathode or when the electrode on the lead is an anode. In some examples, the medical electrical lead is implanted in the substernal space of the patient.

In an example, an impedance signal may be generated between any two electrodes, such as two electrodes on the same lead. As such, the impedance signal may be indicative of the impedance proximate to, for example, the cathode. In other examples, the impedance signal may be indicative of the impedance proximate to the anode. In an example, the electrodes used for impedance measurements may be monopolar, although being monopolar may not be required. In an example, electrodes of different sizes may be used (e.g., the can or a patch may be used in combination with a smaller electrode on a lead). In an example, the impedance tissue proximate the smaller of the electrodes that form the vector may be more prominent in the impedance signal.

In some examples, a medical device may inject a carrier signal between electrodes, e.g., a coil electrode or other electrode on a lead and a housing electrode, and the resulting impedance signal may be indicative of the impedance proximate to the lead electrode. In some examples, the carrier signal is a high frequency carrier signal. The high frequency signals may include frequencies of about 0.1 Hz to about 1 MHz, such as about 4 Hz to about 100 kHz. In other examples, other types of signals may be injected via the same electrodes or other electrodes to facilitate the impedance measurement.

In some examples, the impedance signal may change based on a change in location of the electrode, based on a change in physiology or anatomy, or both. A change in physiology may include a change in the heart's electrical or mechanical activity. The morphology of the impedance signal from the substernal space may vary depending on the location of the electrodes relative to the patient's heart or lungs. By using the techniques described herein, medical device systems may determine information about cardiac events, respiration information, and information normally associate with other types of signals (e.g., other than impedance signals in the substernal space). Such information may aid in cardiac monitoring and cardiac therapy for the patient.

The impedance signal may comprise one or more components. One example of the component is a frequency component. Another example of the component may be morphological component, e.g., a particular impedance signal wave shape, such as an abrupt change in slope. Medical device systems implementing the techniques described herein may determine multiple components from the impedance signal, such as one or more frequency components and/or morphological components. In some examples, medical device systems may compare the impedance signal to signal templates, e.g., morphological templates, to determine a cardiac event. Medical device systems may derive the templates from impedance signals of the patient or of other subjects.

In some examples, a medical device system includes one or more devices. For example, the medical device system may include an extravascular ICD. The extravascular ICD may include or be coupled to a lead (e.g., a substernal lead). In some examples, the impedance signal generated by impedance measurement circuitry of the extravascular ICD may provide increased specificity for determining information about cardiac events. By not directly contacting the heart and with increased specificity, the systems and techniques described herein may be used to provide therapy better suited for the patient and over longer periods of time.

The medical device system may include processing circuitry, e.g., such as processing circuitry of an extravascular ICD, other implantable or external medical device that provides therapy to and/or monitors the patient, or an external device that communicates an implantable medical device that measures impedance. The processing circuitry may identify one or more components of the impedance signal. For example, the processing circuitry may identify a first component correlated to or associated with a cardiac event of the patient's heart. The processing circuitry may determine the cardiac event occurred based on the identification of the first component of the impedance signal. In general, a component of the impedance signal may correspond to, among other things, an amplitude, a frequency, a wavelength, a power or intensity in Fourier space, a slope (e.g., a first order derivative with respect to time), or other morphological characteristic of the signal, another signal characteristic, or any combination thereof. In some examples, the impedance data includes data about conduction volume that may include blood, tissue, mediastinal space, or other data. The processing circuitry may determine heart motion or respiration changes based on the conduction volume, such as determined from the impedance signal.

In some examples, the component is based on or determined by a function. For example, the processing circuitry may determine a moving average of the impedance signal, such as at a fraction of a typical respiration rate (e.g., $\frac{1}{10}$ of the typical respiration rate) to determine a respiration signal (e.g., respiration waveform 310 of FIG. 3B). In some examples, the characteristic is based on or determined by a hardware filter, a software filter, or a combination of the two. The processing circuitry may determine the component. In some examples, the processing circuitry may access a template component, such as stored in a memory of the medical device system, and compare the signal to the template component to identify the characteristic associated with the cardiac event, e.g., the depolarization event.

In an example, processing circuitry may apply one or more filters to the impedance signal. The processing circuitry may detect a cardiac event from the impedance signal by applying a filter (e.g., a first order difference filter such as $x(n)-x(n-1)$, or a second order filter such as $x(n)-x(n-2)$, or a fourth order filter such as $x(n)-x(n-4)$). The processing circuitry may then rectify the filtered signal and apply an adaptive detection threshold to detect the cardiac event. Once the cardiac event is detected, the processing circuitry may determine where the cardiac event is reflected on the impedance signal.

In some examples, the processing circuitry may additionally or alternatively smooth a high-slew cardiac event component away from the impedance signal. The processing circuitry may apply some filtering (e.g., an ultra-low pass filter such as 0.5 Hz low pass) to extract the ultra-low frequency component related to respiration, and the processing circuitry may determine zero-crossings to estimate the respiration cycle and finding peak-peak values during a cycle to determine an estimate of the respiration depth. In addition, the processing circuitry may apply a band-pass filter (e.g., 0.5 Hz-20 Hz) to the difference filtered impedance signal to extract the components related to cardiac motion.

In some examples, the processing circuitry may determine local maximum or local minimum values of the impedance signal. In some examples, the processing circuitry may determine a derivative signal of the impedance signal, and determine zero crossings of the derivative signal. In some examples, the processing circuitry may apply a function or a transform (e.g., a filter function, a Fourier transform, a wavelet transform) to the impedance signal. The processing circuitry may determine a component (e.g., the first component and/or a second component) of the signal based on one or more of the examples described herein. The processing circuitry may compare the component to a threshold value or other criterion to indicate a cardiac event. In some examples, the threshold value or criterion may take the form of a template.

The processing circuitry may determine other information from the impedance signal. For example, the impedance signal morphology may contain information about a cardiac event, a respiration event, pathophysiological events, or other information. Impedance signal information may contain information about organs, such as respiration rate, heart rate, thoracic impedance, or a state of edema in the patient.

In some examples, the processing circuitry may detect cardiac arrhythmias (e.g., ventricular tachycardia, supraventricular tachycardia, ventricular fibrillation, or others), e.g., based on detection of cardiac depolarizations within, or other features of, the impedance signal. In some examples, the processing circuitry may determine that the heart is in normal sinus rhythm (e.g., the processing circuitry may determine a normal EGM based on the impedance signal), e.g., based on detection of cardiac depolarizations within, or other features of, the impedance signal. In some examples, the processing circuitry may determine mechanical cardiac function based on the impedance signal. For example, the processing circuitry may detect mechanical desynchrony, such as may be treated with ATP, using the impedance signal to detect cardiac depolarization and mechanical motion of heart, before an EGM would typically indicate such a patient state. In some examples, the processing circuitry may determine a hemodynamic event or state of the patient such as described further herein.

Although described herein with respect to a medical device system that may include an implantable medical device, the systems and techniques may also be applicable to a delivery system. The delivery system may include an implant tool. For example, the implant tool comprises an elongate tool, a sheath, and a handle. In some examples, the implant tool comprises one or more electrodes, such as on the elongate tool, the sheath, or both. The delivery system may generate the impedance signal and may determine information about cardiac events, alone or in combination with, one or more other medical devices.

Figure 1B:
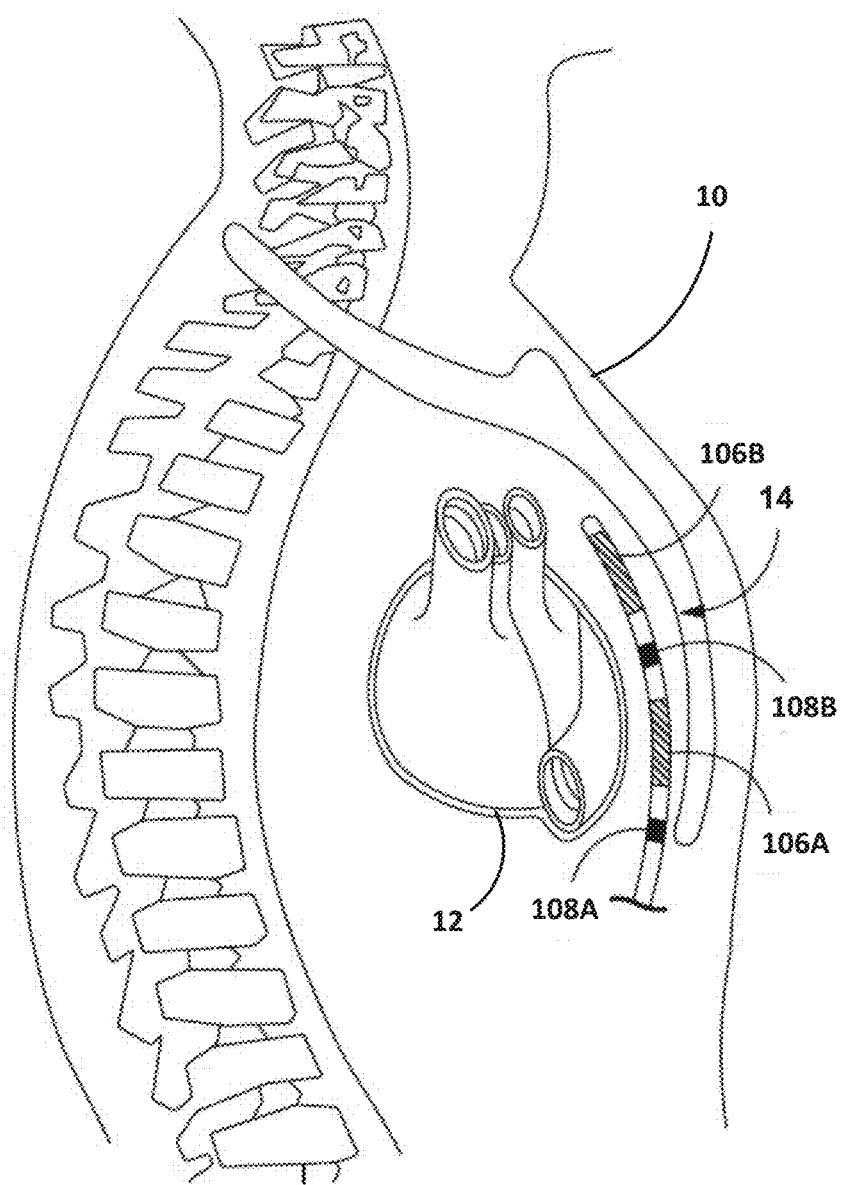
Figure 1C:
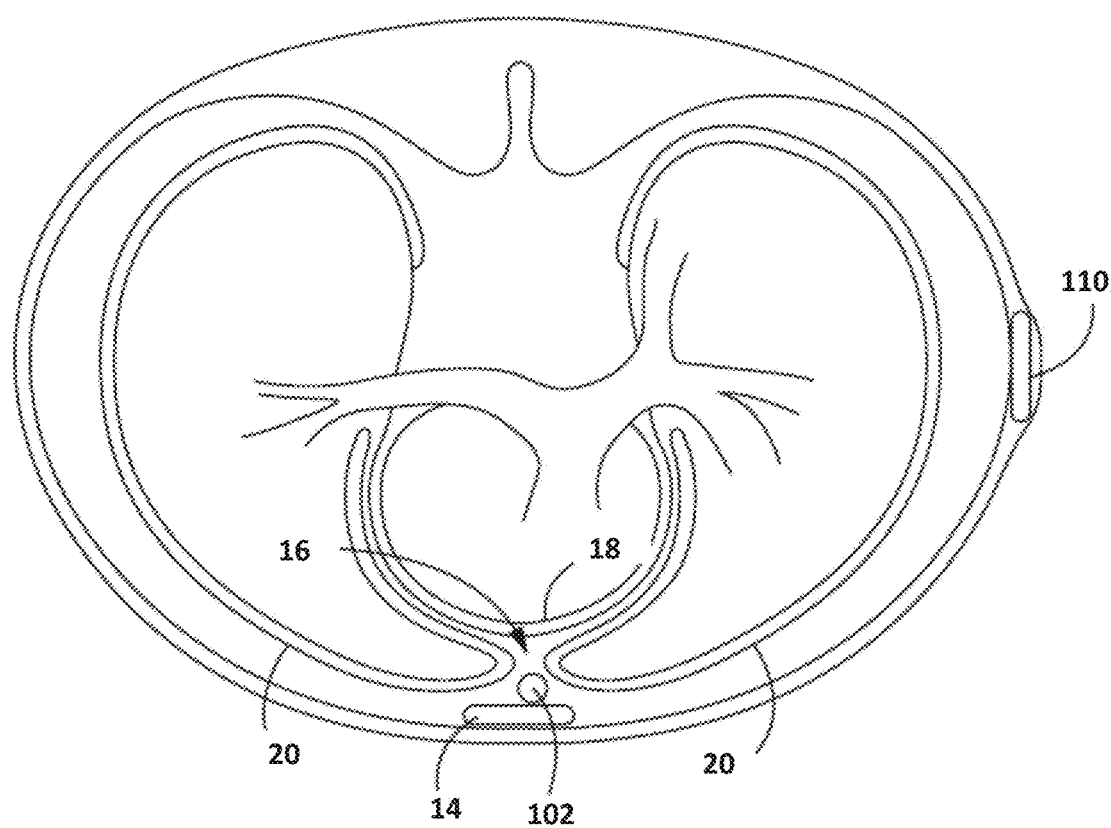

FIGS. 1A-1C are front-view, side-view, and top-view conceptual drawings, respectively, illustrating an example of a medical device system 100 (also referred to as "system 100") in conjunction with a patient 10. In the illustrated example, medical device system 100 is an extravascular ICD system implanted within patient 10. However, these techniques may be applicable to other cardiac systems, including cardiac pacemaker systems, cardiac resynchronization therapy defibrillator (CRT-D) systems, cardioverter systems, or combinations thereof, as well as other stimulation and/or sensing systems, such as neurostimulation systems. In addition, system 100 may not be limited to treatment of a human patient. In alternative examples, system 100 may be implemented in non-human patients, such as primates, canines, equines, pigs, bovines, ovines, and felines. These other animals may undergo clinical or research therapies that may benefit from the subject matter of this disclosure.

In general, systems (e.g., system 100) may include one or more medical devices, leads, external devices, or other components configured for techniques described herein. In the illustrated example, ICD system 100 includes an implantable medical device (IMD) 110, which is an ICD and is referred to hereafter as ICD 110. ICD 110 is connected to at least one implantable cardiac defibrillation lead 102. In some examples, two leads are used. ICD 110 may be configured to provide electrical stimulation to a patient's heart 12, such as to deliver high-energy cardioversion or defibrillation pulses when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 110. In some examples, the systems and techniques described herein may include determining the R-wave information based on the impedance signal, and comparing the R-wave information to the criteria.

ICD 110 may also be configured to provide an impedance signal, e.g., a high frequency carrier signal, between two electrodes coupled to ICD 110. By providing the impedance signal between two electrodes and determining impedance information, information about cardiac events or other physiological information may be determined, as described further herein.

In an example, ICD 110 may comprise impedance measurement circuitry, and may couple one or more electrodes (e.g., communicatively coupled) to the impedance measurement circuitry. ICD 110 and/or another external or implantable device, e.g., external device 130, may comprise processing circuitry configured to identify one or more components of the impedance signal and determine that a physiological event occurred based on the identification of the one or more components. As described further herein, the one or more components may be correlated to or associated with physiological phenomena.

ICD 110 is implanted subcutaneously or submuscularly on the left side of patient 10 above the ribcage. Defibrillation lead 102 may be implanted at least partially in a substernal space, e.g., between the ribcage or sternum 14 and heart 12. In one such configuration, a proximal portion of lead 102 extends subcutaneously from ICD 110 toward sternum 14 and a distal portion of lead 102 extends superior under or below sternum 14 in the anterior mediastinum 16 (FIG. 1C). The anterior mediastinum 16 is bounded laterally by the pleurae 20 (FIG. 1C), posteriorly by the pericardium 18 (FIG. 1C), and anteriorly by the sternum 14. In some instances, the anterior wall of the anterior mediastinum may also be formed by the transversus thoracics and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 102 extends along the posterior side of the sternum 14 substantially within the loose connective tissue or substernal musculature of the anterior mediastinum.

In general, "substernal space" may refer to the region defined by the undersurface between sternum 14 and the body cavity but not including pericardium 18. In other words, the region is posterior to the sternum 14 and anterior to the ascending aorta. The substernal space may alternatively be referred to by the terms "retrosternal space" or "mediastinum" or "infrasternal" as is known to those skilled in the art and includes the region referred to as the anterior mediastinum. For ease of description, the term substernal space will be used in this disclosure, it being understood that the term is interchangeable with any of the other aforementioned terms. Further, although described primarily in the context of a lead in the substernal space, the systems and techniques described herein may be used for lead or device located in the subcutaneous space, or under the skin, or any other location on or within the patient, in other examples.

In this disclosure, the term "extra-pericardial" space may refer to a region around the outer heart surface, but not within the pericardial sac or space. The region defined as the extra-pericardial space includes the gap, tissue, bone, or other anatomical features around the perimeter of, and adjacent to the pericardium.

Lead 102 may be at least partially implanted in other intrathoracic locations, such as other non-vascular, extra-pericardial locations, including the gap, tissue, or other anatomical features around the perimeter of and adjacent to, but not attached to, the pericardium or other portion of the heart and not above the sternum 14 or ribcage. In other examples, lead 102 may be implanted at other extracardiovascular locations. For example, defibrillation lead 102 may extend subcutaneously above the ribcage from ICD 110 toward a center of the torso of patient 10, bend or turn near the center of the torso, and extend subcutaneously superior above the ribcage or sternum 14. Defibrillation lead 102 may be offset laterally to the left or the right of the sternum 14 or located over the sternum 14. Defibrillation lead 102 may extend substantially parallel to the sternum 14 or be angled laterally from the sternum 14 at either the proximal or distal end.

A physician may deliver the lead to the substernal space through a surgical incision created on the skin or tissue adjacent to or below the xiphoid process (also referred to as "subxiphoid") to form an access point to the substernal space, and advanced, e.g., with the aid of a navigation system, to a desired position within the substernal space. The access point may also be formed at the notch that connects the xiphoid process to the sternum. In other examples, the substernal space may also be accessed through the manubrium.

In the case of substernal or subcutaneous electrode of an extravascular ICD system, due to the distance between the heart and electrodes of one or more leads implanted in the patient, to achieve improved pacing, sensing, or defibrillation, the pace/sense electrodes and the defibrillation coil electrode should be positioned in the plane of tissue such that the electrodes are located directly above or proximate the surface of the cardiac silhouette. For example, the one or more electrodes used to deliver pacing pulses should be positioned in a vector over substantially the center of the chamber to be paced to produce the lowest pacing capture thresholds for pacing. Likewise, the one or more electrodes used to sense cardiac electrical activity of the heart should be positioned over substantially the center the chamber to be sensed to obtain the best sensed signal. For shocking purposes, it is preferred to have the defibrillation coil electrode positioned over substantially the center the chamber to be shocked.

In some examples, the systems and techniques described herein include identifying physiological information during implantation of the lead or after implantation is complete. Such information may be used to guide the lead to an appropriate location. For example, the distal portion of the lead with the electrode may be guided to be between the pericardium and the heart. In such examples, the impedance signal indicated by the lead entering the pericardial space may provide a unique impedance morphology.

Defibrillation lead 102 includes an insulative lead body having a proximal end that includes a connector 104 configured to be connected to ICD 110 and a distal portion that includes one or more electrodes. Defibrillation lead 102 also includes one or more conductors that form an electrically conductive path within the lead body and interconnect the electrical connector and respective ones of the electrodes.

In the illustrated example, defibrillation lead 102 includes a defibrillation electrode that includes two sections or segments 106A and 106B (individually or collectively "defibrillation electrode(s) 106"). In some examples, defibrillation lead 102 includes a single contiguous defibrillation electrode 106, rather than segments 106A and 106B. In other examples, lead 102 includes more than one defibrillation electrode, e.g., two defibrillation electrodes such that electrode 106A may be a separate electrode from electrode 106B. The defibrillation electrode 106 is toward the distal portion of defibrillation lead 102, e.g., toward the portion of defibrillation lead 102 extending along the sternum 14. Defibrillation lead 102 is placed below or along sternum 14 such that a therapy vector between defibrillation electrodes 106A or 106B and a housing electrode formed by or on ICD 110 (or other second electrode of the therapy vector) is substantially across a ventricle of heart 12. The therapy vector may, in one example, be viewed as a line that extends from a point on defibrillation electrode 106 (e.g., a center of one of the defibrillation electrode sections 106A or 106B) to a point on the housing electrode of ICD 110. Defibrillation electrode 106 may, in one example, be an elongated coil electrode.

Defibrillation lead 102 may also include one or more sensing electrodes, such as sensing electrodes 108A and 108B (individually or collectively, "sensing electrode(s) 108"), located along the distal portion of defibrillation lead 102. In the example illustrated in FIG. 1A and FIG. 1B, sensing electrodes 108A and 108B are separated from one another by defibrillation electrode 106A. In other examples, however, sensing electrodes 108A and 108B may be both distal of defibrillation electrode 106 or both proximal of defibrillation electrode 106. In other examples, lead 102 may include more or fewer electrodes at various locations proximal or distal to defibrillation electrode 106. In the same or different examples, ICD 110 may be coupled to one or more electrodes on another lead (not shown).

In the example of FIG. 1A, moving distally, sensing electrode 108A may be referred to as a first sensing electrode, electrode 106A may be referred to as a first defibrillation electrode segment, sensing electrode 108B may be referred to as a second sensing electrode, and electrode 106B may be referred to as a second defibrillation electrode segment.

Although referred to herein as "defibrillation electrodes," "defibrillation electrode segments" and "sensing electrodes," electrodes 106, 108 may correspond to, for example, a device other than ICD 110 and/or provide functionality instead of or in addition to defibrillation and sensing. In some examples, "defibrillation electrodes" as used herein may include coil electrodes, that may pace or sense in some instances. In some examples, "sensing electrodes" as used herein may include ring, tip, segmented, or semispherical electrodes, that may pace in some instances.

Lead 102 may be configured in different sizes and shapes, such as may appropriate for purposes (e.g., different patients or different therapies). In some examples, the distal portion of lead 102 may have one or more curved sections, such as shown in FIG. 1A. In some examples, the distal portion of lead 102 may be straight (e.g., straight, or nearly straight). Other lead configurations may be used, such as various electrode arrangements. For example, a sensing electrode may be placed between two defibrillation electrodes or segments, such as described above. In an example, multiple sensing electrodes may be placed between two defibrillation electrodes or segments. In an example, two defibrillation electrodes or segments may not be separated by a sensing electrode. Other arrangements may additionally or alternatively be used.

In an example, the electrode arrangement on lead 102 may correspond to a geometry of lead 102. For example, sensing electrodes may be positioned on relative peaks of a curved lead shape, while defibrillation electrodes may be positioned on relative valleys of the curved lead shape. In an example, sensing electrodes may be positioned on relative valleys of the curved lead shape, while defibrillation electrodes may be positioned on relative peaks of the curved lead shape. In other examples, the distal portion of lead 102 may include branches, biased portions expanding away from a central shaft, or other shapes (e.g., with one or more electrodes disposed on the branches, shaft, or biased portions) that may provide appropriate monitoring information or therapy.

The systems and techniques described herein may be implemented using different types of leads (e.g., as described above or other lead shapes, lead configurations, and the like), including leads designed for different types of therapies (e.g., cardiac defibrillation, cardiac pacing, spinal cord stimulation, or brain stimulation). The systems and techniques described herein may additionally or alternatively be implemented using, for example, delivery systems (e.g., a sheath or an elongate tool) or other devices that may be inserted into a patient (e.g., the substernal space of the patient) to deliver lead 102 or another device. The techniques described herein may be implemented by any device or system that includes electrodes on or within the patient.

In general, for example, ICD system 100 may sense electrical signals, such as via one or more sensing vectors that include combinations of electrodes 108A and 108B and the housing electrode of ICD 110. In some examples, ICD 110 may sense cardiac electrical signals, e.g., cardiac EGMs, using a sensing vector that includes one of the defibrillation electrode sections 106A and 106B and one of sensing electrodes 108A and 108B or a housing electrode of ICD 110. The sensed electrical intrinsic signals may include electrical signals generated by cardiac muscle and indicative of depolarizations and repolarizations of heart 12 at various times during the cardiac cycle. ICD 110 analyzes the electrical signals sensed by the one or more sensing vectors to detect tachyarrhythmia, such as ventricular tachycardia or ventricular fibrillation. In response to detecting the tachyarrhythmia, ICD 110 may begin to charge a storage element, such as a bank of one or more capacitors, and, when charged, deliver one or more defibrillation pulses via defibrillation electrode 106 of defibrillation lead 102 if the tachyarrhythmia is still present. Additionally or alternatively, ICD 110 may deliver pacing therapy, such as via electrodes 106, 108 and or the housing electrode of ICD 110. In an example, the pacing therapy includes antitachycardia pacing (ATP).

In some examples, external device 130 may be a computing device, e.g., used in a home, ambulatory, clinic, or hospital setting, to communicate with ICD 110 via wireless telemetry. Examples of communication techniques used by ICD 110 and external device 130 include radiofrequency (RF) telemetry, which may be an RF link established via Bluetooth, Wi-Fi, or medical implant communication service (MICS), or tissue conduction communication (TCC). The communication may include one-way communication in which one device is configured to transmit communication messages and the other device is configured to receive those messages. The communication may instead include two-way communication in which each device is configured to transmit and receive communication messages.

External device 130 may be configured to carry out all or part of the techniques describes herein. In one example, external device 130 comprises communication circuitry configured to communicate with ICD 110 to receive impedance signals, and processing circuitry configured to detect a physiological event, such as cardiac depolarization or other cardiac electrical event, based on the impedance signal per the techniques described herein. External device 130 may be used to program commands or operating parameters into ICD 110 for controlling its functioning, such as when configured as a programmer for ICD 110. External device 130 may be used to communicate with ICD 110, such as to retrieve data, including device operational data as well as physiological data accumulated in IMD memory, such as information determined based on impedance information sensed by electrodes 106, 108 or the housing electrode according to the techniques described herein. External device 130 may be, as examples, a navigation guidance system, a programmer, external monitor, or consumer device, such as a smartphone. External device 130 may be coupled to a remote patient monitoring system, such as Carelink®, available from Medtronic plc, of Dublin, Ireland.

A user may program or update therapy parameters that define therapy, or perform any other activities with respect to ICD 110, using external device 130. The user may be a physician, technician, surgeon, electrophysiologist, or other healthcare professional. In an example, the user may be patient 10.

Figure 1D:
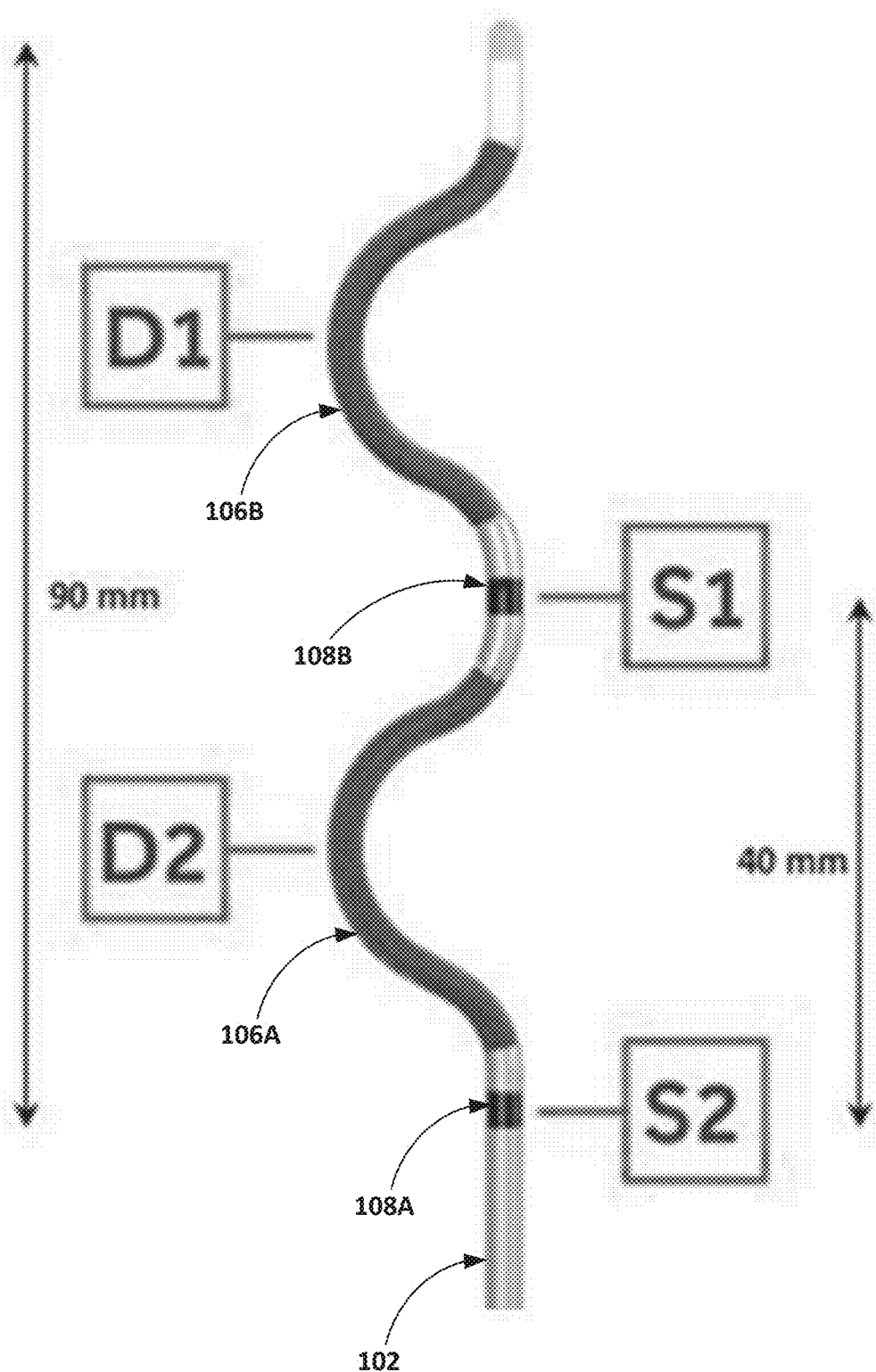
FIG. 1D is an illustrative example configuration of a portion of the medical device system.

FIG. 1D is an illustrative example of a portion of medical device system 100. For example, FIG. 1D includes examples of distances between various elements of the distal portion of lead 102. For example, the curved lead example of FIG. 1D may have a distance of about 40 millimeters between sensing electrodes 108A and 108B. In an example, the lead example may have a distance of about 90 millimeters between a distal end of lead 102 to sensing electrode 108A. In some examples, defibrillation electrode 106B may be referred to as "D1," sensing electrode 108B may be referred to as "S1," defibrillation electrode 106A may be referred to as "D2," and sensing electrode 108A may be referred to as "S2." In general, any suitable distance between any elements of lead 102 may be used. In general, the electrodes of the lead described herein may be arranged in any order or combination of electrodes. For example, there may be two or more sensing electrodes between defibrillation electrodes. Or, in an example, there may be a space separating the defibrillation electrodes, such as separated by an insulated portion of the lead body.

Figure 2A:
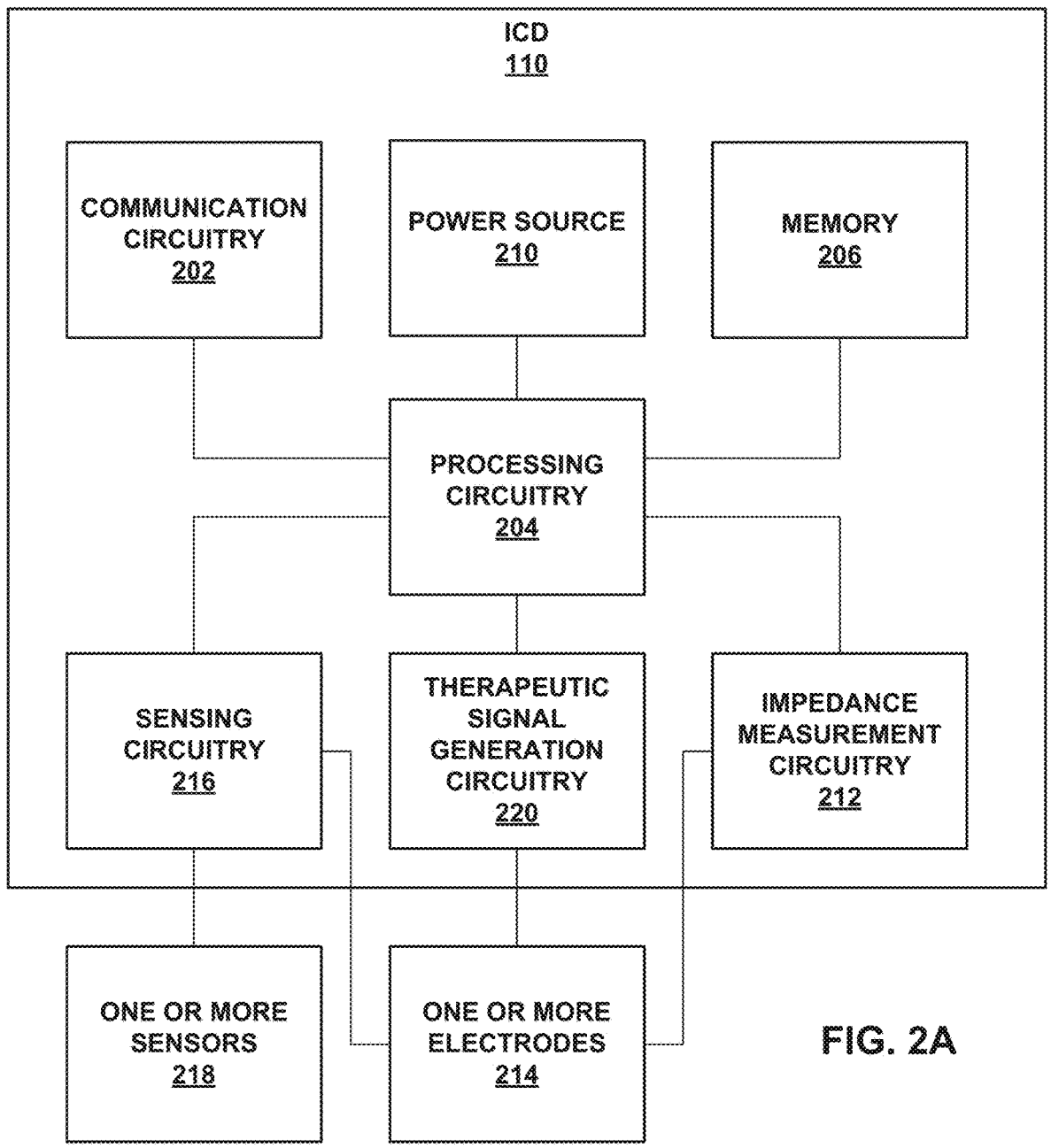
FIG. 2A is a functional block diagram illustrating an example of an implantable medical device configured to acquire an impedance signal according to the techniques of this disclosure.

FIG. 2A is a functional block diagram illustrating an example configuration of ICD 110. In the illustrated example, ICD 110 includes communication circuitry 202, processing circuitry 204, memory 206, impedance measurement circuitry 212, sensing circuitry 216, one or more sensors 218, and therapeutic signal generation circuitry 220. In an example, impedance measurement circuitry is coupled to a plurality of electrodes 214. Electrodes 214 may correspond to electrodes 106, electrodes 108, the housing electrode, electrodes on a delivery sheath or delivery tool, or other electrodes. ICD 110 may include additional components or fewer components. Although described in the context of the example of ICD 110, other implanted or external medical devices may be configured similarly to the configuration of ICD 110 shown in FIG. 2A to implement the impedance sensing techniques of this disclosure but, for example, may not provide therapy and/or other sensing.

Electrodes 214 may comprise ring electrodes, hemispherical electrodes, coil electrodes, helical electrodes, ribbon electrodes, or other types of electrodes, or combinations thereof. Electrodes 214 may be the same type of electrode or different types of electrodes. In some examples electrodes 214 may correspond to electrodes 106 or 108 on lead 102, and additionally or alternatively, may correspond to electrodes on housing of ICD 110.

Communication circuitry 202 includes any suitable hardware, firmware, software, or any combination thereof, for communicating with another device. For example, communication circuitry 202 may be configured to allow ICD 110 to communicate with external device 130, or other devices or systems, in examples in which ICD 110 is not incorporated in such devices or system. Under the control of processing circuitry 204, communication circuitry 202 may receive downlink communications from and send uplink communications to another device with the aid of an antenna (not shown), which may be external, internal, or both. Communication circuitry 202 may include circuitry configured for generating, modulating, receiving, and demodulating a communication signal, e.g., a sinusoidal or pulsatile signal of a desired frequency and amplitude, which may be a RF signal or a TCC signal in some examples. In some examples, communication circuitry 202 may communicate with a local external device, and processing circuitry 204 may communicate with a networked computing device via the local external device and a computer network. In some examples, other devices or systems, such as ICD 110 or external device 130, may include similar communication circuitry, such that there may be a communication link between devices, and data may be transferred, for example, from ICD 110 implanted in patient 10 to a computing device external to patient 10. In an example, communication circuitry 202 is configured to transmit the determination of the occurrence of the cardiac event to external device 130.

Processing circuitry 204 may perform the techniques described herein for determining the occurrence of the cardiac event in the patient. Processing circuitry 204 may include fixed function circuitry, programmable processing circuitry, or both. Processing circuitry 204 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 204 may include multiple components, such as any combination of one or more microprocessors, one or more controllers, one or more DSPs, one or more ASICs, or one or more FPGAs, as well as other discrete or integrated logic circuitry. The functions attributed to processing circuitry 204 herein may be embodied as software, firmware, hardware, or any combination thereof.

Memory 206 includes computer-readable instructions that, when executed by processing circuitry 204, cause ICD 110 and processing circuitry 204 to perform various functions attributed to ICD 110 and processing circuitry 204 as described herein. Memory 206 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. In some examples, memory 206 accumulates physiological data, such as sensed physiological signals, impedance signals or components thereof, or other data.

ICD 110 may include circuitry, such as may correspond to impedance measurement circuitry 212 in some examples, that may generate a waveform (e.g., a voltage waveform or a current waveform). The circuitry may deliver a signal via two or more of electrodes 214, and determine an impedance signal based on the delivery of the signal via the electrodes. The circuitry may be configured to generate one of a current or voltage signal, deliver the signal via a selected two or more of electrodes 214, and measure the resulting other of current or voltage. Processing circuitry 204 may determine an impedance signal based on the delivered current or voltage and the measured voltage or current. For example, such circuitry may be configured to inject a pulsatile waveform or a sinusoidal current waveform, such as of an amplitude below a threshold for capturing tissue.

In some examples, impedance measurement circuitry 212 may include one or more voltage or current sources, wave-shaping circuitry, switches, filters, amplifiers sample-and-hold circuitry, or analog-to-digital converters. As such, ICD 110 may sample and hold a voltage value at a node of circuitry with ICD 110. The impedance signal may be filtered before the circuitry samples and holds the voltage value at the node, and the circuitry may also convert the sample to a digital signal. As such, impedance may be calculated based on the injected current amplitude and the sampled voltage.

Impedance measurement circuitry 212 may generate a plurality of impedance signals. Impedance measurement circuitry 212 may be coupled to the one or more electrodes 214. Each of the impedance signals may include components indicative of a cardiac event, or of different types of physiological events. Impedance measurement circuitry 212 may output the generated impedance signals to processing circuitry 204. Processing circuitry 204 identifies one or more components of each impedance signal. Lead 102 may be placed such that a therapy vector between a defibrillation electrode on the lead and a housing or can electrode is substantially across the ventricle of the heart, or in another desired location within the substernal space, such as described herein.

In some examples, ICD 110 includes one or more sensors 218. In some examples, one or more sensors 218 may include, as examples: an accelerometer, which may be configured to generate a signal indicative of patient activity and/or posture; a heart sound sensor, which may be an accelerometer, microphone, or piezoelectric sensor, configured to generate a signal that includes heart sounds; electrodes in addition or alternative to one or more electrodes 214; or a temperature sensor. One or more sensors 218 may be coupled to sensing circuitry 216, which may be configured to generate signals based on the sensed phenomena. In some examples, sensing circuitry 216 generates an accelerometer signal. In some examples sensing circuitry 216 generates an EGM signal. In some examples, sensing circuitry 216 generates a heart sounds signal. Sensing circuitry 216 may comprise amplifiers, filters, analog-to-digital converters, and other circuitry configured to generate and condition the signals for receipt by processing circuitry 204.

As illustrated in FIG. 2A, sensing circuitry 216 may also be coupled to electrodes 214 and may, for example, receive cardiac electrical signals from selected combinations of two or more electrodes 214, and sense cardiac events attendant to depolarization and repolarization of cardiac tissue. Sensing circuitry 216 may include one or more sensing channels, each of which may be selectively coupled to respective combinations of electrodes 214 to detect electrical activity of heart 12, e.g., one or more ventricular sensing channels. Each sensing channel may be configured to amplify, filter and rectify the cardiac electrical signal received from selected electrodes coupled to the respective sensing channel to detect cardiac events, e.g., R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 216 may output an indication to processing circuitry 204 in response to sensing a cardiac event in a chamber of interest, e.g., an R-wave. In this manner, processing circuitry 204 may receive detected cardiac event signals corresponding to the occurrence of detected R-waves. Indications of detected R-waves may be used by processing circuitry 204 for detecting ventricular arrhythmia episodes, as well as to determine the timing of cardiac pacing. Sensing circuitry 216 may also pass one or more digitized cardiac EGM signals to processing circuitry 204 for analysis.

In an example, processing circuitry 204 may determine a measurement of the impedance signal. The measurement may be a value as measured in ohms, degrees, or another measure of the impedance signal. Processing circuitry 204 may determine that the measurement of the impedance signal satisfies a criterion. For example, the criterion may correspond to a threshold value. The threshold value may be a minimum or maximum threshold value. If the measurement meets or exceeds the threshold, then processing circuitry 204 may provide an indication to the user via external device or a networked device. If needed, a warning indication may be an indication designed to immediately warn or alert the user of a potential undesirable cardiac state, such as fibrillation. Another criterion example may include a particular slope threshold of impedance over time, and the measurement of the impedance may be a slope of the signal. In other examples, the measurement of the impedance signal and the criterion are based on multiple elements, such as a function, or other information such as may be gathered from an imaging system. In some examples, multiple criteria may be used. For example, processing circuitry 204 may use a second criterion as confirmation of the measurement of the impedance signal satisfying the first criterion.

Therapeutic signal generation circuitry 220 may be coupled to one or more electrodes 214. In some examples, therapeutic signal generation circuitry 220 may be configured to deliver a therapy shock to heart 12 based on a determination that patient 10 is hemodynamically non-stable. For example, if patient 10 has a fibrillation, ICD 110 may deliver therapy to heart 12 via electrodes 214. In some examples, therapeutic signal generation circuitry 220 may be configured to deliver anti-tachycardia pacing to heart 12 based on a determination that patient 10 is hemodynamically stable (e.g., not requiring immediate defibrillation shock, but may have tachyarrhythmia). Therapeutic signal generation circuitry 220 includes charging circuitry, one or more charge storage devices, such as one or more high voltage capacitors and in some examples one or more low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapeutic signal generation circuitry 220 according to control signals received from processing circuitry 204. Processing circuitry 204 may include various timers or counters that control when ATP or other cardiac pacing pulses are delivered.

In some examples, ICD 110 may take the form of a Reveal LINQ® Insertable Cardiac Monitor (ICM), available from Medtronic plc, of Dublin, Ireland. In some examples, ICD 110 may take the form of a Medtronic® Micra® self-contained pacemaker that is designed to be implanted internally, for example within a chamber of the heart of the patient, and in various examples requires no external leads coupled to the device in order to provide pacing and electrical stimulation to the heart. In some examples, the medical device system described herein may include one or more different types of devices described herein (e.g., an ICD and a Reveal LINQ® device).

Figure 2B:
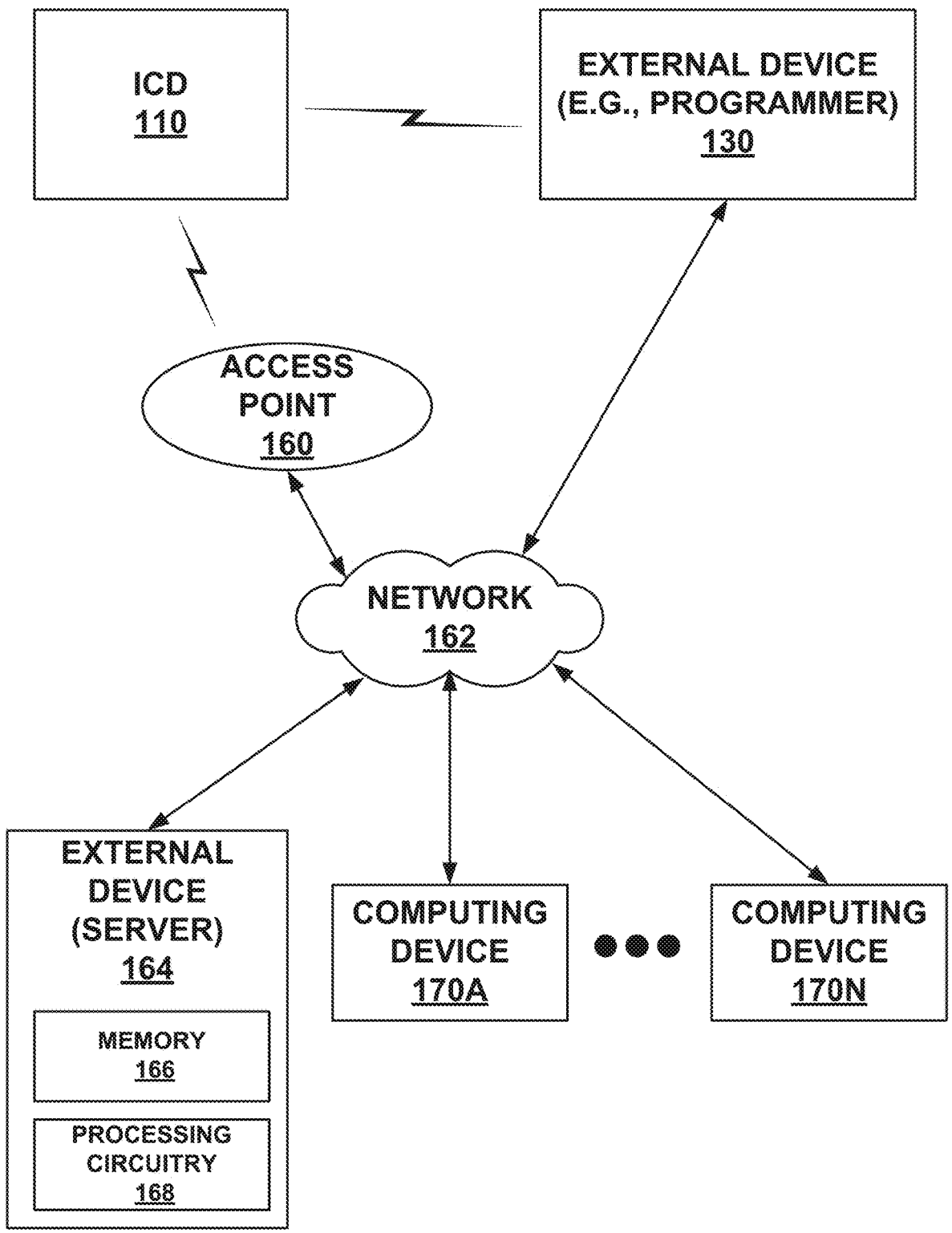
FIG. 2B is a functional block diagram illustrating an example system that includes external computing devices, such as a server and one or more other computing devices, that are coupled to the ICD shown in FIG. 2A via a network.

FIG. 2B is a functional block diagram illustrating an example system that includes external computing devices, such as a server 164 and one or more other computing devices 170A-170N, that are coupled to ICD 110 and external device 130 via a network 162. In this example, ICD 110 may use its communication circuitry 202 to, e.g., at different times and/or in different locations or settings, communicate with programmer 130 via a first wireless connection, and to communication with an access point 160 via a second wireless connection. In the example of FIG. 2B, access point 160, external device 130, server 164, and computing devices 170A-170N are interconnected, and able to communicate with each other, through network 162.

Access point 160 may comprise a device that connects to network 162 via any of a variety of connections, such as telephone dial-up, digital subscriber line (DSL), or cable modem connections. In other examples, access point 160 may be coupled to network 162 through different forms of connections, including wired or wireless connections. In some examples, access point 160 may be co-located with patient 10. Access point 160 may interrogate ICD 110, e.g., periodically or in response to a command from patient 10 or network 162, to impedance signal data or other operational data from ICD 110. Access point 160 may provide the retrieved data to server 164 via network 162.

In some cases, server 164 may be configured to provide a secure storage site for data that has been collected from ICD 110 and/or external device 130, such as the Internet. In some cases, server 164 may assemble data in web pages or other documents for viewing by trained professionals, such as clinicians, via computing devices 170A-170N. The illustrated system of FIG. 2B may be implemented, in some aspects, with general network technology and functionality similar to that provided by the Medtronic CareLink® Network developed by Medtronic plc, of Dublin, Ireland.

In some examples, one or more of access point 160, server 164, or computing devices 170 may be configured to perform, e.g., may include processing circuitry configured to perform, some or all of the techniques described herein relating to determining the occurrence of a cardiac event based on an impedance signal. In the example of FIG. 2B, server 164 includes a memory 166 to store impedance signal data received from ICD 110, and processing circuitry 168, which may be configured to provide some or all of the functionality ascribed to processing circuitry 204 of IMD 110 herein.

FIGS. 3A and 3B illustrate graphs of examples including impedance signals. The top signal illustrated in FIG. 3A includes an electrogram (EGM) signal 302. The bottom signal illustrated in FIG. 3A includes an impedance signal 304. The top signal illustrated in FIG. 3B includes an EGM signal 306. The bottom signal illustrated in FIG. 3B includes an impedance signal 308. The horizontal axis, although not demarcated in the graphs illustrated in FIGS. 3A and 3B, is time, such as measured in seconds. The vertical axis for the EGM signals 302 and 306, although not demarcated in the graphs illustrated in FIGS. 3A and 3B, is voltage, such as measured in microvolts. The vertical axis for the impedance signals 304 and 308, although not demarcated in the graphs illustrated in FIGS. 3A and 3B, is impedance, such as measured in Ohms.

Impedance signal 304 may correspond to a signal determined, for example, from a sensing electrode vector including at least one electrode in the substernal space (e.g., from electrode 108A to electrode 108B, or from one of electrodes 108 to a housing electrode). EGM signal 304 may be determined from the same sensing vector or a different sensing vector. Again, the techniques of this disclosure may be implemented using electrodes positioned anywhere on or within the body.

FIG. 3A includes corresponding components 320 in the EGM signal 302 and impedance signal 304. Components 320 may be seen as generally aligned in time. As such, the corresponding components 320 may be indicative of the same physiological event, such as a cardiac event. Processing circuitry of medical device system 100, e.g., processing circuitry 204 of ICD 110, may implement the techniques of this disclosure to determine that the cardiac event occurred based on the component 320 of impedance signal 304 independent of the EGM signal 302. In other words, by using the techniques described herein, EGM information (e.g., information normally determined by an EGM signal) may be determined based on impedance signal information without requiring the EGM signal itself. The systems and techniques described herein may not require an EGM signal to detect cardiac events, e.g., cardiac depolarizations or other cardiac events, although information from both an impedance signal and other signals such as the EGM signal may be used to determine that such an event has occurred in some examples.

Component 340 may be a relatively broad peak component 340 of impedance signal 304. In some examples, the impedance oscillations and morphological features (e.g., width, peak amplitude, or area under the curve), of broad peak 340 may be indicative of contraction and relaxation of the heart, which may be correlated to volume changes of the heart. A volume change of the heart may correspond to a change in the amount of space the heart occupies inside the patient and the amount of fluid, e.g., blood, in that space. In general, processing circuitry 204 may identify one or more components of the impedance signal 304. One such component may be component 340. Based on component 340, processing circuitry 204 may be configured to determine that a cardiac contraction has occurred, or to estimate other parameters, such as stroke volume, ejection fraction, or other parameters that indicate heart failure status or the mechanical effectiveness of the heart. In some examples, more than one cardiac event may be determined to have occurred. For example, processing circuitry 204 may determine, based on a component spanning a longer time, that both cardiac contraction and relaxation have occurred, such as based on component 340.

In the example illustrated in FIG. 3B, corresponding components 330 and 332 may again be seen as aligned temporally between EGM signal 306 and impedance signal 308. Processing circuitry may determine a respiration waveform 310 based on impedance signal 308, such as by determining a signal trend over time. In some examples, processing circuitry 204 may apply functions, such as rolling averages or low-pass filters to signal 308 to determine a signal component or the respiration waveform 310.

FIGS. 3A and 3B are examples that include components that may be identified using an impedance signal in the substernal space. Processing circuitry may identify other components. An impedance signal component from the substernal space may correlated to one or more of many physiological phenomena or events (e.g., atrial depolarization, the beginning of atrial systole, an end ventricular diastolic volume time, a ventricular depolarization, an isovolumetric contraction, the beginning of ventricular repolarization, an isovolumetric relaxation, a ventricular filling event, or others). An impedance signal component from the substernal space may be correlated to or associated with one or more heart sounds, in some examples. An impedance signal component from the substernal space may be correlated to or associated with pressures in various chambers of the heart at various points during the cardiac cycle. Some events may have relatively short durations, such as about 0.1 seconds for an atrial systole event, 0.3 seconds for a ventricular systole event, or other similar events. Some events may have relatively longer durations, such as multiple respiration cycles over tens of seconds. In some examples, processing circuitry 204 may track cardiac events over time, such as to determine trends.

Figure 3C:
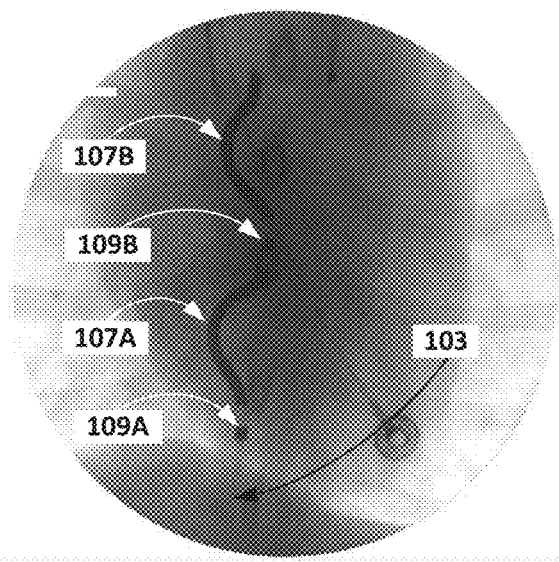
FIGS. 3C-3F are images of example leads placed in substernal locations.
Figure 3D:
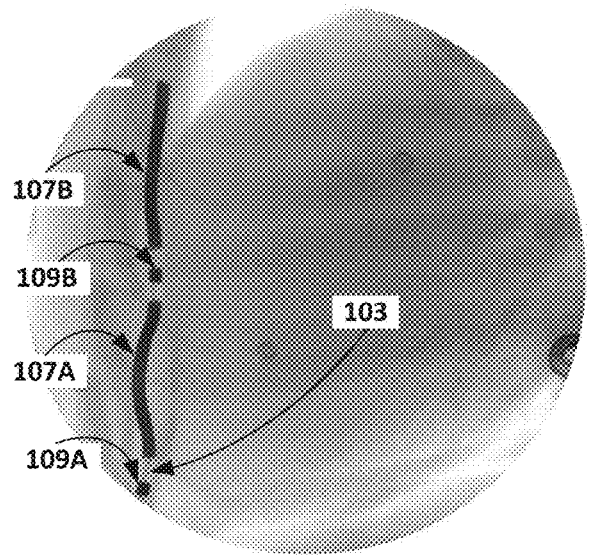

FIGS. 3C-3F are images of example leads placed in substernal locations. The leads illustrated in FIGS. 3C-3F may have the electrode configuration illustrated in FIG. 1D. The examples of FIGS. 3C and 3D are images of a lead 103 placed in a substernal location relative to a canine heart. Electrodes 107A, 107B, 109A, and 109B may be positioned on a distal portion of lead 103. The example of FIG. 3C is an alternative frontal radiographic projection (AP projection) of the lead, and the example of FIG. 3D is a left anterior oblique projection (LAO projection) of the lead and the heart. The cardiac EGM waveform 302 and impedance waveform 304 of FIG. 3A were collected using electrodes 109A and 109B of lead 103, with 109A as the cathode.

Figure 3E:
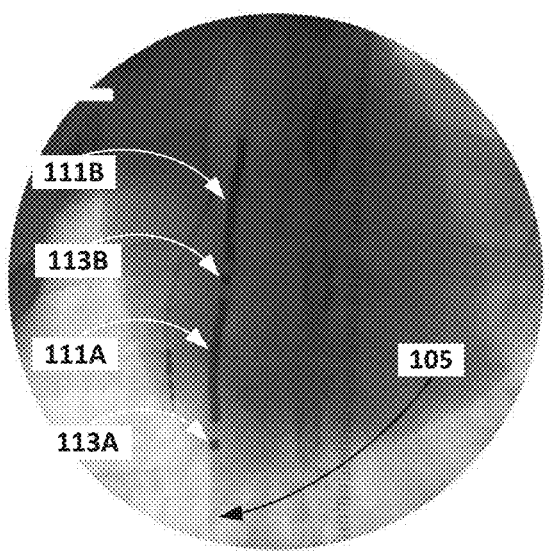
Figure 3F:
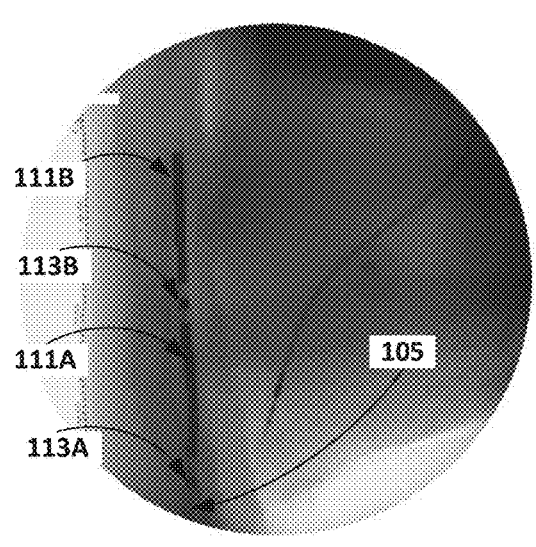

FIGS. 3E and 3F are images of a lead 105 place in a substernal location relative to a pig heart. Electrodes 111A, 111B, 113A, and 113B may be positioned on a distal portion of lead 105. The example of FIG. 3E is an AP projection of the lead, and the example of FIG. 3D is an LAO projection of the lead and the heart. The cardiac EGM waveform 306 and impedance waveform 308 of FIG. 3B were collected using electrodes 113A and 113B of lead 105, with 113A as the cathode.

Figure 4A:
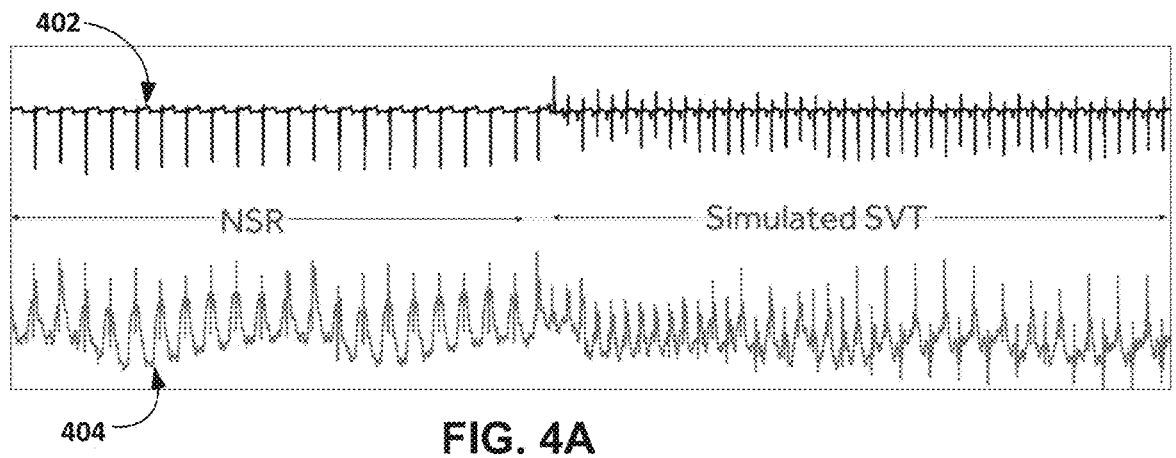
FIGS. 4A-4C illustrate graphs of example physiological signals, including impedance signals.
Figure 4B:
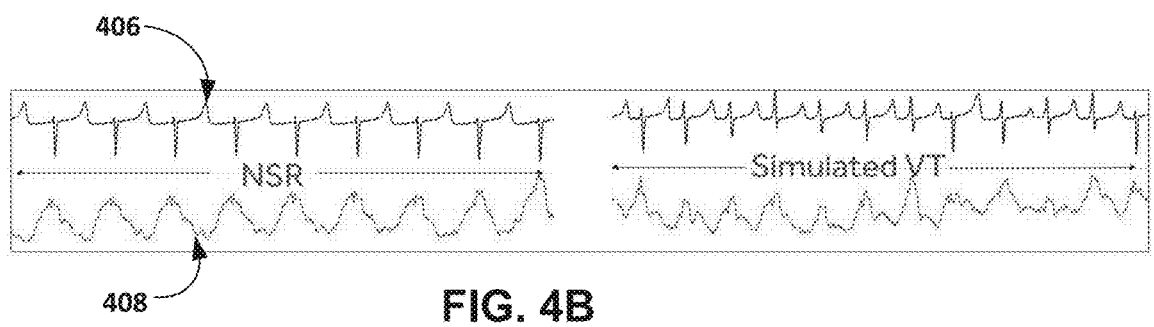
Figure 4C:
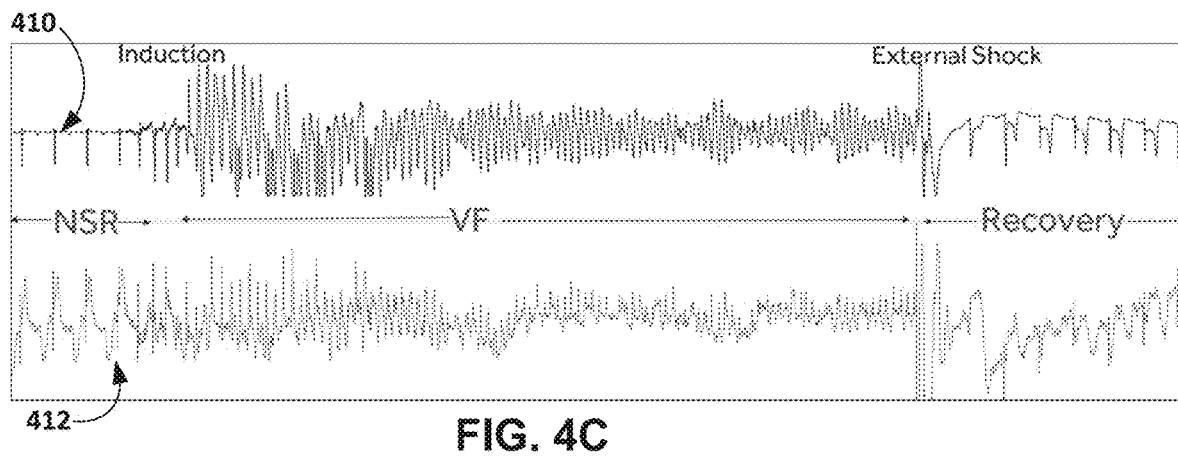

FIGS. 4A-4C illustrate graphs of example physiological signals, including impedance signals. The examples of FIGS. 4A-4C may correspond to EGM (top) and impedance (bottom) signals determine from a pig heart. In the example of FIG. 4A, EGM signal 402 and impedance signal are illustrated in normal sinus rhythm (NSR) (left) and simulated supraventricular tachycardia (SVT) (right). The example of FIG. 4A may correspond to an S1-S2 vector.

In the example of FIG. 4B, EGM signal 406 and impedance signal 408 are illustrated in NSR (left) and simulated VT (right). The example of FIG. 4B may correspond to S1-S2 vector.

In the example of FIG. 4C, EGM signal 410 and impedance signal 412 are illustrated in NSR (left), VF (middle), and recovery (right). The example of FIG. 4B may correspond to an S1-S2 vector.

In an example, FIG. 4C illustrates the approximate location on the graph when VF was induced in the pig, and when an external shock was applied. The example of FIG. 4C may correspond to an S1-S2 vector.

In the examples of FIGS. 4A-4C, processing circuitry may determine impedance information, such as determined from signals 402, 406, and 410. For example, processing circuitry may determine heart motion, respiration, and EGM information. One or more vectors may be selected to determine an appropriate signal. One or more components illustrate in the examples of FIGS. 4A-4C may correspond to various cardiac events, such as described further herein.

In general, as described herein, the medical device system 100 may use a source frequency (e.g., 1 to 100 kHz) at a sampling rate (e.g., 256 samples/second) to determine heart motion, respiration, or EGM information from the impedance signal.

Figure 5:
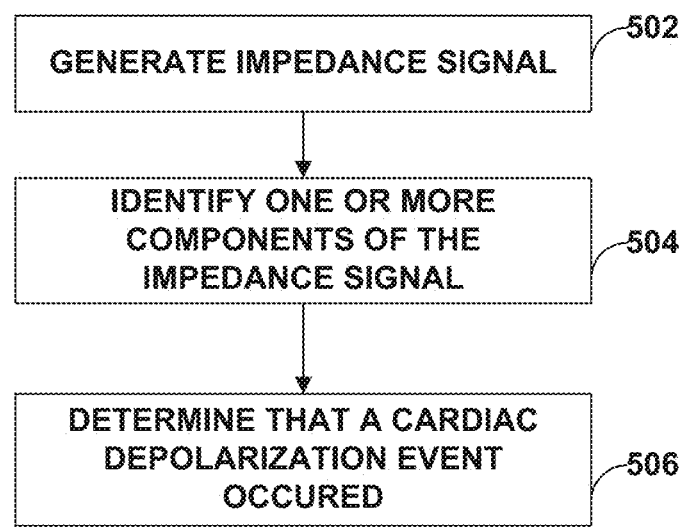
FIG. 5 is a flow chart depicting an example method of determining that a cardiac event has occurred based on an impedance signal according to some examples of this disclosure.

FIG. 5 is a flow chart depicting an example method of determining that a cardiac event has occurred according to some examples of this disclosure. The method is described as being performed by ICD 110, including by processing circuitry 204 of ICD 100, as described herein. In some examples, some or all of the example method may be performed by other devices, such as by processing circuitry of external device 130 or server 164.

According to the illustrated example, impedance measurement circuitry 212 may generate an impedance signal, such as illustrated in FIGS. 3A and 3B (502). The impedance signal may correspond to a real impedance or a reactive impedance. In general, impedance may be represented as a complex quantity, such as including a real part (e.g., resistance) and an imaginary part (e.g., reactance). Processing circuitry 204 may identify one or more components from the impedance signal (504). For example, a first component may correspond to the cardiac event. Processing circuitry 204 may determine that the cardiac event occurred based on the identified first component of the impedance signal (506).

In some examples, filtering may be performed, such as by processing circuitry 204, after generating the impedance signal. A Fourier transform may be performed on the impedance signal, impedance peaks may be identified, filters may be applied, or other processing techniques may be used. In some examples, a 10-hertz low pass filter is applied, and then a Fourier transform is performed.

As described herein, ICD 110 may measure impedance and determine cardiac activity (e.g., cardiac motion, cardiac mechanical events, or cardiac electrical events) based on the measured impedance. ICD 110 may determine a cardiac event based on the impedance signal alone, or in some examples, in combination with one or more other signals (e.g., a heart sounds signal, a three-axis accelerometer signals, or others). In some examples, ICD 110 includes or is coupled to a substernal lead, and ICD 110 may determine cardiac events with greater specificity. ICD 110 may reliably deliver appropriate therapy, such as ATP or defibrillation, because ICD 110 better monitors cardiac activity.

The systems and techniques described herein may provide and/or supplement wellness therapy for patient 10. In an example, ICD 110 is configured to determine when to shock heart 12, such as based on determining cardiac activity. ICD 110 may determine cardiac activity based on impedance sensing, such as described herein, and/or heart sounds, three-axis accelerometer signals, or EGM signals. In some examples, ICD 110 determines a patient hemodynamic state (e.g., an index of patient hemodynamics or a patient hemodynamic log) based on these signals and/or other information. ICD 110 may be configured to process these signals and/or other information and determine parameters (e.g., components of signals). ICD 110 may monitor the patient hemodynamic state and thus guide therapy triage or delivery.

In some examples, ICD 110 is configured to deliver therapy based on a confirmation that the defibrillation therapy is appropriate (e.g., when the patient's hemodynamic state is compromised). In an example, ICD 110 determines a rate of cardiac depolarizations based on an EGM signal, ICD 110 determines a rate of cardiac depolarizations based on an impedance signal, and then compares the rates. Based on a result of the comparison, if both rates of both signals provide the basis for defibrillation (e.g., the difference in rates is less than or equal to a threshold and both satisfy a VF criteria), then ICD 110 may deliver defibrillation therapy. If the rate of cardiac depolarizations based on the impedance signal does not confirm the EGM rate (e.g., the difference between the rates is greater than the threshold), then ICD 110 may be configured to deliver ATP, such as to avoid higher energy therapy. In this manner, the comparison of the rates of the cardiac depolarizations in the EGM signal and the rates of cardiac depolarizations in the impedance signal serve as the criterion for determining the patient's hemodynamic state. In other examples, ICD 110 may determine that therapy is appropriate using the regularity or morphology of the first component in addition to or instead of rate of the first component of the impedance signal. For example, ICD 110 may determine cycle lengths between each of the first components of the impedance signal and determine that defibrillation therapy is appropriate (e.g., patient is hemodynamically unstable) when the cycle lengths are irregular (e.g., A of B cycle lengths are outside a range) or the morphology of the first component is irregular (e.g., X of Y morphologies do not match a template morphology). Otherwise, ICD 110 may determine to deliver anti-tachycardia pacing or no therapy. Thus, rate, regularity and/or morphology of the first component of the impedance signal may serve as criterion for determining the patient's hemodynamic state. In some examples, ICD 110 may monitor the cardiac cycle based on the impedance signal and deliver therapy at appropriate times.

In other examples, ICD 110 may activate or initiate acquisition of the impedance signal based on the cardiac events identified within the EGM. For example, ICD 110 may determine a rate based on the cardiac events identified within the EGM, determine the rate is greater than a threshold tachyarrhythmia rate, and initiate acquisition of the impedance signal in response to the rate being greater than the threshold tachyarrhythmia rate. This would reduce the amount of battery consumption needed to acquire and analyze the impedance signal.

ICD 110 may be configured to monitor disease progression. For example, ICD 110 may measure the cardiac electrical activity (e.g., via EGM) and mechanical activity (e.g., via impedance and/or heart sounds), determine biological phenomena based on the activity (e.g., electromechanical delay), and monitor the patient's heart disease progress based on the determined biological phenomena. In an example, ICD 110 may monitor for decompensation of the patient's heart.

In some examples, ICD 110 is configured to determine whether pacing therapy capture occurs, e.g., after ICD 110 initiates ATP, for example. ICD 110 may determine whether capture occurs (e.g., whether pacing leads to depolarization of the ventricles) based on EGM information determined from the impedance signal.

In some examples, ICD 110 is configured to determine a posture of patient 10. For example, ICD 110 may comprise an accelerometer sensor and circuitry configured to generate an accelerometer signal. ICD 110 may automatically adjust a pacing capture threshold. In an example, ICD 110 may determine a mechanical capture threshold under different postures of patient 10. ICD 110 may determine if capture has occurred based on mechanical cardiac signals (e.g., information determined from the impedance signal or heart sounds information). ICD 110 may automatically test the pacing capture threshold under different postures. The systems and techniques described herein may include posture modulated auto adjusting pacing capture threshold, which may improve device longevity (e.g., such as may be particularly helpful for patients needing chronic pacing therapy).

In some examples, the systems and techniques may be used as a diagnostic tool for respiration or cardiac monitoring (e.g., such as EKG monitoring).

The following numbered clauses demonstrate one or more aspects of this disclosure.

Clause 1: In one example, a method comprises generating, by impedance measurement circuitry coupled to an electrode an impedance signal indicating impedance proximate to the electrode; identifying, by processing circuitry, a first component of the impedance signal, the first component correlated to a cardiac depolarization event; and determining, by the processing circuitry, that the cardiac depolarization event occurred based on the identification of the first component of the impedance signal.

Clause 2: In some examples of the method of clause 1, the method further comprises determining, by the processing circuitry, a patient hemodynamic state based on the impedance signal.

Clause 3: In some examples of the method of clause 2, the method further comprises determining the patient hemodynamic state comprises determining a patient hemodynamic state based on the impedance signal and at least one of a heart sound signal, an electrogram signal, or an accelerometer signal.

Clause 4: In some examples of the method of clause 3, the method further comprises comparing, by the processing circuitry, the patient hemodynamic state to a criterion, and determining, by the processing circuitry, that the patient hemodynamic state is non-stable based on a result of the comparison.

Clause 5: In some examples of the method of clause 4, the method further comprises delivering, by therapeutic signal generation circuitry, a therapy shock to a heart of the patient based on the determination that the patient hemodynamic state is non-stable.

Clause 6: In some examples of the method of any of clauses 3-5, the method further comprises comparing, by the processing circuitry, the patient hemodynamic state to a criterion, and determining, by the processing circuitry, that the patient hemodynamic state is stable based on a result of the comparison.

Clause 7: In some examples of the method of clause 6, the method further comprises delivering, by therapeutic signal generation circuitry, anti-tachycardia pacing to the heart of the patient based on the determination that the patient hemodynamic state is stable.

Clause 8: In some examples of the method of any of clauses 3-7, the method further comprises determining, by the processing circuitry, that the heart has a tachyarrhythmia based on the electrogram signal, and confirming, by the processing circuitry, that the heart has the tachyarrhythmia based on the first component of the impedance signal, and wherein the confirmation is based on one or more of a rate, a regularity, or a morphology of the first component.

Clause 9: In some examples of the method of any of clauses 3-8, the method further comprises determining, by the processing circuitry, that cardiac fibrillation is predicted to occur based on the impedance signal and at least one of the heart sound signal, the electrogram signal, or the accelerometer signal.

Clause 10: In some examples of the method of any of clauses 1-9, the method further comprises determining, by the processing circuitry, a patient heart disease state based on the impedance signal and at least one of a heart sound signal, an electrogram signal, or an accelerometer signal; and monitoring, by the processing circuitry, the patient heart disease state over time.

Clause 11: In some examples of the method clause 10, monitoring the patient heart disease state includes monitoring cardiac decompensation.

Clause 12: In some examples of the method of any of clauses 1-11, the method further comprises sensing, with sensing circuitry, an electrogram signal, determining that the cardiac depolarization event occurred based on the electrogram signal, and confirming, by the processing circuitry, that the cardiac depolarization event occurred based on the impedance signal.

Clause 13: In some examples of the method of any of clauses 1-12, the method further comprises delivering, by therapeutic signal generation circuitry, a pacing pulse to the heart, wherein identifying the first component of the impedance signal comprises identifying the first component subsequent to the delivery of the pacing pulse, and wherein determining that the cardiac depolarization event occurred comprises determining that the pacing pulse captured the heart.

Clause 14: In some examples of the method of any of clauses 1-13, the method further comprises determining, by the processing circuitry, a posture of the patient based information on at least one of the impedance signal, a heart sound signal, or an accelerometer signal, wherein the accelerometer signal is generated by an accelerometer placed in or on a heart of the patient; and determining a pacing capture threshold for the posture of the patient based on the information.

Clause 15: In some examples of the method of any of clauses 1-14, the electrode is implanted in the substernal space.

Clause 16: In some examples of the method of any of clauses 1-15, the cardiac depolarization event is a ventricular depolarization event.

Clause 17: In some examples of the method of any of clauses 1-16, the first component of the impedance signal comprises at least one of an abrupt valley or slope in the impedance signal.

Clause 18: In some examples of the method of any of clauses 1-17, identifying the first component comprises applying, by the processing circuitry, a filter to the impedance signal.

Clause 19: In some examples of the method of any of clauses 1-18, identifying the first component comprises determining, by the processing circuitry, a derivative of the impedance signal.

Clause 20: In some examples of the method of any of clauses 1-19, identifying the first component comprises applying, by the processing circuitry, a transform function to the impedance signal.

Clause 21: In some examples of the method of clause 20, the transform function comprises a Fourier transform function.

Clause 22: In some examples of the method of any of clauses 1-21, the cardiac depolarization comprises a cardiac electrical event.

Clause 23: In some examples, a medical device system comprises: an electrode; impedance measurement circuitry coupled to the electrode, the impedance measurement circuitry configured to generate an impedance signal indicating impedance proximate to the electrode; and processing circuitry configured to: identify a first component of the impedance signal, the first component correlated to a cardiac depolarization event; and determine that the cardiac depolarization event occurred based on the identification of the first component of the impedance signal.

Clause 24: In some examples of the medical device system of clause 23, the processing circuitry is configured to determine a patient hemodynamic state based on the impedance signal.

Clause 25: In some examples of the medical device system of clause 24, the processing circuitry is configured to determine the patient hemodynamic state based on the impedance signal and at least one of a heart sound signal, an electrogram signal, or an accelerometer signal.

Clause 26: In some examples of the medical device system of clause 25, the processing circuitry is configured to: compare the patient hemodynamic state to a criterion, and determine that the patient hemodynamic state is non-stable based on a result of the comparison.

Clause 27: In some examples of the medical device system of clause 26, the medical device system further comprises therapeutic signal generation circuitry configured to deliver a therapy shock to a heart of the patient, wherein the processing circuitry is configured to control the therapeutic signal generation circuitry to deliver the shock based on the determination that the patient hemodynamic state is non-stable.

Clause 28: In some examples of the medical device system of any of clauses 25-27, the processing circuitry is configured to compare the patient hemodynamic state to a criterion, and determine that the patient hemodynamic state is stable based on a result of the comparison.

Clause 29: In some examples of the medical device system of clause 28, the medical device system further comprises therapeutic signal generation circuitry configured to deliver anti-tachycardia pacing to the heart of the patient, wherein the processing circuitry is configured to control the therapeutic signal generation circuitry based on the determination that the patient hemodynamic state is stable.

Clause 30: In some examples of the medical device system of any of clauses 25-29, the processing circuitry is configured to determine that the heart has a tachyarrhythmia based on the electrogram signal, and confirming that the heart has the tachyarrhythmia based on the first component of the impedance signal, and wherein the confirmation is based on one or more of a rate, a regularity, or a morphology of the first component.

Clause 31: In some examples of the medical device system of any of clauses 25-30, the processing circuitry is configured to determine that cardiac fibrillation is predicted to occur based on the impedance signal and at least one of the heart sound signal, the electrogram signal, or the accelerometer signal.

Clause 32: In some examples of the medical device system of any of clauses 25-31, the processing circuitry is configured to: determine a patient heart disease state based on the impedance signal and at least one of a heart sound signal, an electrogram signal, or an accelerometer signal; and monitor the patient heart disease state over time.

Clause 33: In some examples of the medical device system of clause 32, the processing circuitry is configured to monitor cardiac decompensation.

Clause 34: In some examples of the medical device system of any of clauses 23-33, the medical device system further comprises sensing circuitry configured to sense an electrogram signal, and wherein the processing circuitry is configured to determine that the cardiac depolarization event occurred based on the electrogram signal, and confirm that the cardiac depolarization event occurred based on the impedance signal.

Clause 35: In some examples of the medical device system of any of clauses 23-34, the processing circuitry is configured to determine a posture of the patient based information on at least one of the impedance signal, a heart sound signal, or an accelerometer signal determine a pacing capture threshold for the posture of the patient based on the information.

Clause 36: In some examples of the medical device system of any of clauses 23-35, the electrode is implanted in the substernal space.

Clause 37: In some examples of the medical device system of any of clauses 23-36, the cardiac depolarization event is a ventricular depolarization event.

Clause 38: In some examples of the medical device system of clauses 23-37, the first component of the impedance signal comprises at least one of an abrupt valley or slope in the impedance signal.

Clause 39: In some examples of the medical device system of any of clauses 23-38, the processing circuitry is configured to identify the first component by applying a filter to the impedance signal.

Clause 40: In some examples of the medical device system of any of clauses 23-39, the processing circuitry is configured to identify the first component by determining a derivative of the impedance signal.

Clause 41: In some examples of the medical device system of any of clauses 23-40, the processing circuitry is configured to identify the first component by applying a transform function to the impedance signal.

Clause 42: In some examples of the medical device system of clause 41, the transform function comprises a Fourier transform function.

Clause 43: In some examples of the medical device system of any of clauses 23-42, the electrode is implanted in the substernal space, the medical device system further comprising an implantable cardiac defibrillator (ICD), the ICD comprising the impedance measurement circuitry.

Clause 44: In some examples of the medical device system of clause 43, the ICD comprises the processing circuitry.

Clause 45: In some examples of the medical device system of any of clauses 23-44, the cardiac depolarization comprises a cardiac electrical event.

Clause 46: In some examples a method comprises: generating, by impedance measurement circuitry coupled to an electrode, an impedance signal indicating impedance proximate to the electrode; identifying, by processing circuitry, a component of the impedance signal, the component correlated to a cardiac event; and determining, by the processing circuitry, that the cardiac event occurred based on the identification of the first component of the impedance signal.

Clause 47: In some examples a method comprises any method described herein, or any combination of the methods described herein.

Clause 48: In some examples a method comprises any combination of the methods of any of clauses 1-22 or 46.

Clause 49: In some examples a system comprises means for performing the method of any of clauses 1-22 or 46.

Clause 50: In some examples a non-transitory computer-readable storage medium comprises instructions stored thereon that, when executed by processing circuity, cause the processing circuitry to perform the method of any of clauses 1-22 or 46.

The examples described herein may be combined in any permutation or combination.

Various aspects of the disclosure have been described. These and other aspects are within the scope of the following claims.

What is claimed is:

1. A medical device system comprising:
an electrode;
impedance measurement circuitry coupled to the electrode, the impedance measurement circuitry configured to generate an impedance signal indicating impedance proximate to the electrode;
therapeutic signal generation circuitry configured to generate and deliver an electrical stimulation; and
processing circuitry configured to:
identify a plurality of cardiac events within the impedance signal based on a determination that a measurement of the impedance signal satisfies at least one criterion;
determine a rate of the plurality of cardiac events identified within impedance signal;
detect a cardiac arrhythmia based on the rate of the plurality of cardiac events identified within the impedance signal; and
control the therapeutic signal generation circuitry to generate the electrical stimulation therapy in response to detection of the cardiac arrhythmia.

2. The medical device system of claim 1, wherein the processing circuitry is further configured to:
determine one or more of a regularity of the identified plurality of cardiac events or a morphology of the identified plurality of cardiac events; and
detect the cardiac arrhythmia based on the one or more of the regularity or the morphology of the identified plurality of cardiac events.

3. The medical device system of claim 1, wherein the processing circuitry is configured to:
detect a change in at least one of an amplitude or a slope in the impedance signal that exceeds a respective threshold; and
identify one of the plurality of cardiac events in response to detecting the change in at least one of the amplitude or the slope of the impedance signal that exceeds the respective threshold.

4. The medical device system of claim 1, wherein the processing circuitry is configured to:
process the impedance signal using one or more of a filter, a transform function, or a derivative; and
analyze the processed impedance signal to detect the plurality of cardiac events.

5. The medical device system of claim 1, further comprising sensing circuitry configured to sense an electrogram signal, wherein the rate of the cardiac events identified within the impedance signal is a first rate of first cardiac events, wherein the processing circuitry is configured to:
identify a second plurality of cardiac events within the electrogram signal;
detect a cardiac arrhythmia based on the second plurality of identified cardiac events; and
confirm the detected cardiac arrhythmia based on the first plurality of cardiac events within the impedance signal.

6. The medical device system of claim 5, wherein the processing circuitry is further configured to:
determine a second rate based on the second plurality of identified cardiac events;
determine the second rate is greater than a threshold tachyarrhythmia rate; and
initiate the impedance measurement circuitry to begin obtaining the impedance signal in response to the rate being greater than the threshold tachyarrhythmia rate.

7. The medical device system of claim 5, wherein the processing circuitry is configured to:
determine a second rate of the second cardiac events within the electrogram signal;
compare the first rate and the second rate;
confirm the detected cardiac arrhythmia based on the comparison of the first rate and the second rate; and
control the therapeutic signal generation circuitry to deliver the electrical stimulation in response to the confirmation.

8. The medical device system of claim 5, wherein the processing circuitry is configured to:
determine a second rate based on the second plurality of identified cardiac events;
determine the second rate is greater than a threshold tachyarrhythmia rate;
initiate the impedance measurement circuitry to begin obtaining the impedance signal in response to the second rate being greater than the threshold tachyarrhythmia rate;
compare the first rate and the second rate;
confirm the detected cardiac arrhythmia based on the comparison of the first rate and the second rate; and
control the therapeutic signal generation circuitry to deliver the electrical stimulation in response to the confirmation.

9. The medical device system of claim 5, wherein the processing circuitry is configured to confirm the detected cardiac arrhythmia based on one or more of the rate, a regularity or a morphology of the first plurality of cardiac events within the impedance signal.

10. The medical device system of claim 1, wherein the processing circuitry is configured to:
determine a patient hemodynamic state;
control the therapeutic signal generation circuitry to deliver a shock when the determined patient hemodynamic state is non-stable; and
control the therapeutic signal generation circuitry to deliver anti-tachycardia pacing when the determined patient hemodynamic state is stable.

11. The medical device system of claim 10, wherein the processing circuitry is configured to determine the patient hemodynamic state based on the impedance signal and at least one of a heart sound signal, an electrogram signal, or an accelerometer signal.

12. A method comprising:
generating an impedance signal indicating impedance proximate an electrode;
identifying a plurality of cardiac events within the impedance signal based upon a determination that a measurement of the impedance signal satisfies at least one criterion;
determining a rate of the plurality of cardiac events identified within the impedance signal;
detecting a cardiac arrhythmia based on the rate of the plurality of identified cardiac events within the impedance signal; and
controlling the therapeutic signal generation circuitry to generate the electrical stimulation therapy in response to detecting cardiac arrhythmia.

13. The method of claim 12, wherein detecting the cardiac arrhythmia comprises:
determining one or more of a regularity of the identified plurality of cardiac events or a morphology of the identified plurality of cardiac events; and detecting the cardiac arrhythmia based on the one or more of the regularity or the morphology of the identified plurality of cardiac events.

14. The method of claim 12, wherein identifying the plurality of cardiac events within the impedance signal comprises:
   detecting a change in at least one of an amplitude or a slope in the impedance signal that exceeds a respective threshold; and
   identifying one of the plurality of cardiac events in response to detecting the change in at least one of the amplitude or the slope of the impedance signal that exceeds the respective threshold.

15. The method of claim 12, wherein identifying a plurality of cardiac events comprises:
   identifying the plurality of cardiac events by processing the impedance signal using one or more of a filter, a transform function, or a derivative; and
   analyzing the processed impedance signal to detect the plurality of cardiac events.

16. The method of claim 12, wherein the rate of the cardiac events identified within the impedance signal is a first rate of first cardiac events, the method further comprising:
   identifying a second plurality of cardiac events within the electrogram signal; and
   detecting a cardiac arrhythmia based on the second plurality of identified cardiac events;
   wherein detecting a cardiac arrhythmia based on the plurality of identified cardiac events within the impedance signal comprises confirming the detected cardiac arrhythmia based on the first plurality of cardiac events within the impedance signal.

17. The method of claim 16, further comprising:
   determining a second rate based on the second plurality of identified cardiac events;
   determining the second rate is greater than a threshold tachyarrhythmia rate; and
   initiating the impedance measurement circuitry to begin obtaining the impedance signal in response to the second rate being greater than the threshold tachyarrhythmia rate.

18. The method of claim 16, further comprising:
   determining a second rate of the second cardiac events within the electrogram signal;
   comparing the first rate and the second rate; and
   confirming the detected cardiac arrhythmia based on the comparison of the first rate and the second rate;
   wherein controlling the therapeutic signal generation circuitry to generate the electrical stimulation therapy in response to detecting cardiac arrhythmia comprises controlling the therapeutic signal generation circuitry to deliver the electrical stimulation in response to the confirmation.

19. The method of claim 16, further comprising:
   determining a second rate based on the second plurality of identified cardiac events;
   determining the second rate is greater than a threshold tachyarrhythmia rate;
   initiating the impedance measurement circuitry to begin obtaining the impedance signal in response to the second rate being greater than the threshold tachyarrhythmia rate;
   comparing the first rate and the second rate; and
   confirming the detected cardiac arrhythmia based on the comparison of the first rate and the second rate;
   wherein controlling the therapeutic signal generation circuitry to generate the electrical stimulation therapy in response to detecting cardiac arrhythmia comprises controlling the therapeutic signal generation circuitry to deliver the electrical stimulation in response to the confirmation.

20. The method of claim 16, wherein confirming the detected cardiac arrhythmia based on the first plurality of cardiac events within the impedance signal comprises confirming the detected cardiac arrhythmia based on one or more of the first rate, a regularity or a morphology of the first plurality of cardiac events within the impedance signal.

21. The method of claim 12, further comprising:
   determining a patient hemodynamic state;
   wherein controlling the therapeutic signal generation circuitry to generate the electrical stimulation therapy in response to detecting cardiac arrhythmia comprises:
      controlling the therapeutic signal generation circuitry to deliver a shock when the determined patient hemodynamic state is non-stable; and
      controlling the therapeutic signal generation circuitry to deliver anti-tachycardia pacing when the determined patient hemodynamic state is stable.

22. The method of claim 21, wherein determining the patient hemodynamic state comprises determining the patient hemodynamic state based on the impedance signal and at least one of a heart sound signal, an electrogram signal, or an accelerometer signal.

23. A medical device system comprising:
   an electrode;
   impedance measurement circuitry coupled to the electrode, the impedance measurement circuitry configured to generate an impedance signal indicating impedance proximate to the electrode; and
   processing circuitry configured to:
      analyze at least one of an amplitude and a slope in the impedance signal;
      detect a change in at least one of the amplitude or the slope in the impedance signal that exceeds a respective threshold; and
      detect a cardiac event in response to detecting the change in at least one of the amplitude or the slope of the impedance signal that exceeds the respective threshold.

* * * * *